United States Patent [19]

Hanasaki et al.

[11] Patent Number: 5,498,593
[45] Date of Patent: Mar. 12, 1996

[54] THIADIAZOLE DERIVATIVES AND HERBICIDE COMPOSITIONS CONTAINING THE SAME

[75] Inventors: Yasuaki Hanasaki; Kazuaki Tsukuda; Hiroyuki Watanabe; Kenji Tsuzuki; Mitsuyuki Murakami; Noritoshi Niimi, all of Shinnanyo, Japan

[73] Assignee: TOSOH Corporation, Yamaguchi, Japan

[21] Appl. No.: 401,771

[22] Filed: Mar. 10, 1995

Related U.S. Application Data

[62] Division of Ser. No. 27,579, Mar. 5, 1993, which is a continuation of Ser. No. 633,348, Dec. 27, 1990, abandoned, which is a continuation-in-part of Ser. No. 570,638, Aug. 22, 1990, abandoned.

[30] Foreign Application Priority Data

| Aug. 22, 1989 | [JP] | Japan | 1-215489 |
| Oct. 30, 1989 | [JP] | Japan | 1-279725 |
| Nov. 22, 1989 | [JP] | Japan | 1-302258 |
| Dec. 25, 1989 | [JP] | Japan | 1-332875 |

[51] Int. Cl.$^6$ .......................... A01N 43/72; C07D 285/10
[52] U.S. Cl. .......................... 504/264; 548/135
[58] Field of Search .................. 548/135; 504/261

[56] References Cited

U.S. PATENT DOCUMENTS

| 4,555,521 | 11/1985 | Engel et al. ............................. 514/362 |

FOREIGN PATENT DOCUMENTS

| 0019742 | 12/1980 | European Pat. Off. ............... 548/135 |
| 1925956 | 11/1969 | Germany ................................. 548/135 |
| 3822371 | 2/1990 | Germany ................................. 548/135 |

OTHER PUBLICATIONS

J. Heterocyclic Chem., 16, 1009, Sulfur Nitride . . . Acetylenes (1,2), 1979, Mataka et al.
CA115:29342s Preparation . . . herbicides. Hanasaki et al., p. 780, 1991.
CA116:36257s Synegistic . . . rice. Niimi et al., pp. 268–269, 1992.
Chemical Abstracts vol. 94, Feb. 2, 1981 No. 5.

*Primary Examiner*—Joseph K. McKane
*Attorney, Agent, or Firm*—Nixon & Vanderhye

[57] ABSTRACT

Thiadiazole derivatives with excellent herbicidal effectiveness, wide herbicidal spectrum and excellent selectivity are disclosed. The thiadiazole derivatives are represented by one of the formula [I]–[IV].

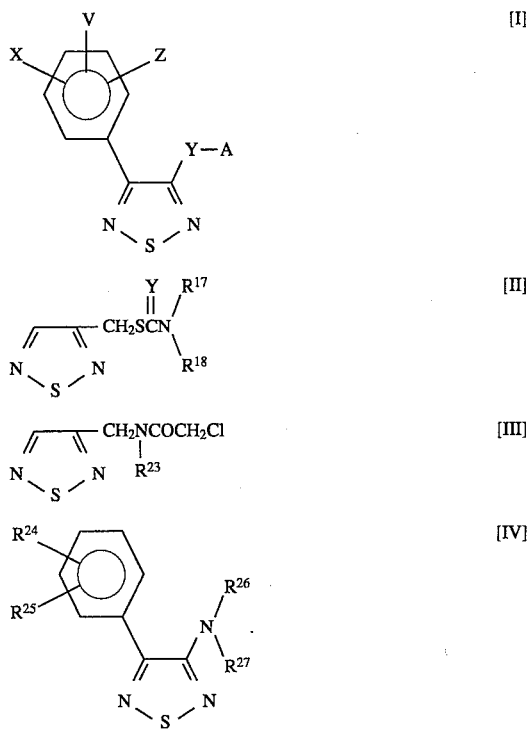

8 Claims, No Drawings

THIADIAZOLE DERIVATIVES AND HERBICIDE COMPOSITIONS CONTAINING THE SAME

This is a Division of application Ser. No. 08/027,579, filed Mar. 5, 1993, pending which is a continuation of Ser. No. 07/633,348, filed Dec. 27, 1990, abandoned; which is a continuation-in-part of Ser. No. 07/570,638, filed Aug. 22, 1990, now abandoned.

BACKGROUND OF THE INVENTION

I. Field of the Invention

The present invention relates to thiadiazol derivatives and herbicide compositions containing the same.

II. Description of the Related Art

A number of herbicides have been developed and used. However, in general, the conventional herbicides have a problem in that their herbicidal effectiveness is unsatisfactory, herbicidal spectrum is narrow or crops are damaged by the herbicides.

It is known that 2,1,3-benzothiadiazole derivatives as well as 1,2,4- and 1,3,4- thiadiazole derivatives have herbicidal activities. However, it has not been known that 1,2,5-thiadiazole derivatives have herbicidal activities.

SUMMARY OF THE INVENTION

An object of the present invention is to provide a novel compound which exhibits high herbicidal activities and which does not damage the crops, as well as a herbicide composition containing the novel compound as an effective ingredient.

The present inventors intensively studied to find that specific 1,2,5-thiadiazole derivatives exhibit high herbicidal activities against wide variety of weeds while they do not substantially damage the crops, to complete the present invention.

That is, the present invention provides a thiadiazole derivative represented by the formula [I]

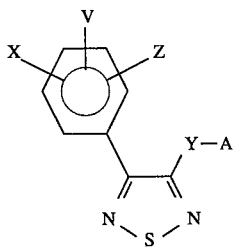

[wherein Y represents oxygen or sulfur; X represents hydrogen, halogen, lower alkyl, lower haloalkyl, lower alkoxy, hydroxy or nitro; V and Z, the same or different, represent halogen, lower alkyl, lower haloalkyl, lower alkoxy, hydroxy or nitro; A represents hydrogen, lower alkyl, lower alkenyl, lower alkynyl, alkoxyalkyl which may be substituted with alkoxy, alkylthioalkyl —SO$_2$R$^1$ (wherein R$^1$ represents lower alkyl which may be substituted with halogen, phenyl which may be substituted with lower alkyl, or amino which is substituted with lower alkyl),

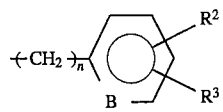

(wherein n represents 0 or 1, B represents CH or nitrogen, R$^2$ and R$^3$, the same or different, represent hydrogen, halogen, lower alkoxy, nitro or lower alkyl which may be substituted with halogen), —SiR$^4$R$^5$R$^6$ (wherein R$^4$, R$^5$ and R$^6$, the same or different, represent lower alkyl), —CHR$^7$COR$^8$ (wherein R$^7$ represents hydrogen or lower alkyl, R$^8$ represents hydroxy or amino which may be substituted with lower alkyl and/or with phenyl), —C(=W)OR$^9$ (wherein W represents oxygen or sulfur, R$^9$ represents alkyl which may be substituted with halogen; alkoxyalkyl, benzyl, phenyl, tetrahydrofurfuryl or alkylideneamino), —COR$^{10}$ (wherein R$^{10}$ represents lower alkyl; cycloalkyl; or phenyl which may be substituted with halogen, lower alkyl, lower haloalkyl, lower alkoxy, nitro or with cyano; —C(=W)NR$^{11}$R$^{12}$ (wherein W represents oxygen or sulfur, R$^{11}$ and R$^{12}$, the same or different, represent hydrogen, lower alkyl, cycloalkyl, lower alkoxy, alkoxyalkyl, phenyl which may be substituted with alkoxy,

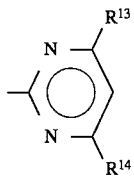

(wherein R$^{13}$ and R$^{14}$, the same or different, represent hydrogen, halogen, lower alkyl or lower alkoxy)), or R$^{11}$ and R$^{12}$ cooperatively form

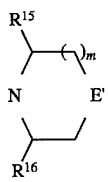

(wherein E$^1$ represents —CH$_2$— or oxygen, m represents 0 or 1, R$^{15}$ and R$^{16}$, the same or different, represent hydrogen or lower alkyl)].

The present invention also provides a thiadiazole derivative represented by the formula [II]

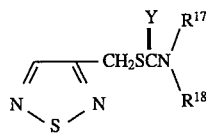

[wherein Y represents oxygen or sulfur, R$^{17}$ and R$^{18}$, the same or different, liner or branched lower alkyl, cycloalkyl or lower alkoxyalkyl, or R$^{17}$ and R$^{18}$ cooperatively form

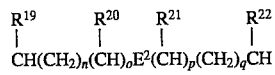

(wherein E$^2$ represents —CH$_2$—, nitrogen or oxygen; n, o, p and q, the same or different, represent an integer of 0– 2; R$^{19}$, R$^{20}$, R$^{21}$ and R$^{22}$, the same or different, represent hydrogen or lower alkyl)].

The present invention further provides a thiadiazole derivative represented by the formula [III]

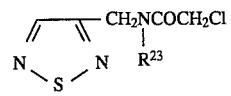

(wherein R$^{23}$ represents phenyl which is substituted with $C_1$–$C_6$ linear or branched alkyl, branched $C_1$–$C_8$ alkenyl or cycloalkenyl which may be substituted with $C_1$–$C_6$ linear or branched alkyl).

The present invention still further provides a thiadiazole derivative represented by the formula [IV]

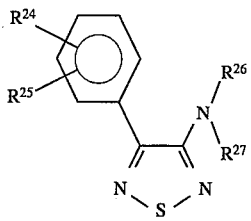

[wherein $R^{24}$ and $R^{25}$, the same or different, represent hydrogen or halogen; $R^{26}$ and $R^{27}$, the same or different, represent hydrogen, lower alkyl, —$COR^{28}$ (wherein $R^{28}$ represents lower alkyl or amino group which may be substituted with lower alkyl), or $R^{26}$ and $R^{27}$ cooperatively form phthaloyl group].

The present invention also provides a process for preparing a thiadiazole derivative represented by the formula [V]

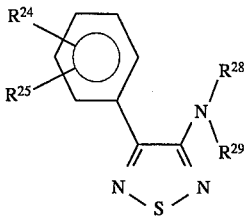

[wherein $R^{24}$ and $R^{25}$ represent the same meaning as in formula [IV]; $R^{28}$ and $R^{29}$, the same or different, represent hydrogen or $C_1$–$C_6$ lower alkyl] comprising reacting a thiadiazole derivative represented by the formula [VI]

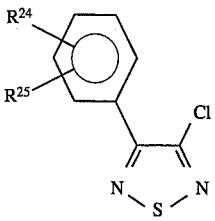

(wherein $R^{24}$ and $R^{25}$ represent the same meaning as in formula [IV]) with an amine represented by the formula [VII]

$NHR^{28}R^{29}$ (wherein $R^{28}$ and $R^{29}$ represent the same meaning as in formula [V]).

The present invention still further provides a process for preparing a thiadiazole derivative represented by the formula [VIII]

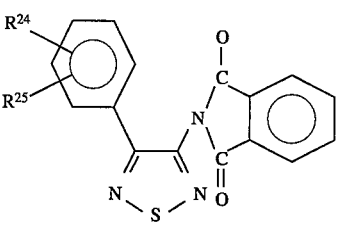

(wherein $R^{24}$ and $R^{25}$ represent the same meaning as in formula [IV]) comprising reacting the thiadiazole derivative represented by above-described formula [VI] with potassium phthalimide.

The present invention still further provides a process for preparing a thiadiazole derivative represented by the formula [IX]

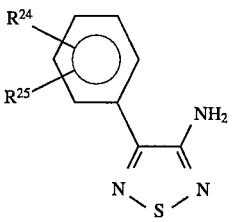

(wherein $R^{24}$ and $R^{25}$ represent the same meaning as in formula [IV]) comprising hydrolyzing said thiadiazole derivative represented by the above-described formula [VIII].

The present invention also provides herbicide compositions comprising a herbicidally effective amount of one of said thiadiazole derivatives of the present invention in an agriculturally acceptable carrier.

By the present invention, novel compounds with excellent herbicidal activities and wide herbicidal spectrum and process for preparing the same, as well as herbicide compositions containing the same as an effective ingredient were provided. The herbicide compositions of the present invention can inhibit the growth of various weeds from before the germination to the growth phase thereof. The herbicide compositions of the present invention have high safety, that is, they do not substantially damage useful crops. Thus, the herbicide composition of the present invention may effectively be used for inhibiting the growth of weeds in paddy fields and in the fields of various crops, vegetables, fruits and mulberry, as well as for inhibiting the growth of weeds in the ground other than field. The herbicide compositions of the present invention are especially effective for inhibiting the growth of weeds in paddy fields.

DETAILED DESCRIPTION OF THE PREFERRED EMBODIMENTS

As mentioned above, according to a first aspect of the present invention, the thiadiazole derivatives represented by the formula [I] are provided. It should be noted that the term "lower" means $C_1$–$C_6$ in this specification and claims unless otherwise specified.

The thiadiazole derivatives represented by the formula [I] may be prepared by reacting a corresponding amino acid amide or a hydrogen halide salt thereof represented by the formula [X] with sulfur monochloride or thionyl chloride according to the method described in Journal of Organic Chemistry, p. 2823 (1967).

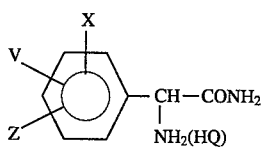

(wherein X, V and Z represent the same meaning as in formula [I], and Q represents halogen).

This reaction may usually be carried out in a solvent at 20°–100° C. for 1–24 hours.

Preferred examples of the solvent which may be used in this reaction may include aromatic hydrocarbons such as benzene and toluene; ethers such as tetrahydrofuran; halogenated hydrocarbons such as chloroform; and polar solvents such as nitromethane, acetonitrile and N,N-dimethylformamide.

The ratio of the reactants may usually be one equivalent of the amino acid amide to 3–4 equivalents of the sulfur monochloride or thionyl chloride.

The thiadiazole derivatives of the formula [I] may also be prepared by reacting a thiadiazole derivative represented by the formula [XI] with A—Q (wherein A represents the same meaning as in formula [I] and Q' represents halogen), $R^9OC(=O)R^9$ (wherein $R^9$ represents the same meaning as in formula [I], or with $R^{10}C(=O)OC(=O)R^{10}$ (wherein $R^{10}$ represents the same meaning as in formula [II]).

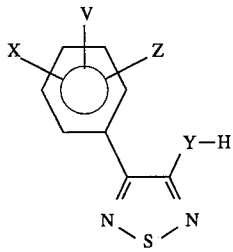

[XI]

(wherein X, Y, Z and V represent the same meaning as in formula [I]).

This reaction may usually be carried out in a solvent and in the presence of a base at 0°–150° C. for several minutes to 48 hours.

Preferred examples of the solvent which may be used in this reaction may include ketones such as acetone and methylethyl ketone; aromatic hydrocarbons such as benzene, toluene and xylene; ethers such as diethyl ether, tetrahydrofuran and dioxane; halogenated hydrocarbons such as dichloromethane, chloroform, carbon tetrachloride, dichloroethane and chlorobenzene; tertially amines such as pyridine, triethylamine and N,N-dimethylaniline; polar solvents such as acetonitrile, N,N-dimethylformamide, dimethylsulfoxide, 1,3-dimethyl-2-imidazolidinone and hexamethyl phosphoric triamide.

Preferred examples of the base which may be used in the reaction may include, organic bases such as pyridine, triethylamine and N,N-dimethylaniline; inorganic bases such as sodium hydroxide, potassium hydroxide, sodium carbonate, potassium carbonate and sodium hydride; and alkaline metal alkoxides such as sodium methoxide and sodium ethoxide.

Usually, 1–2 equivalents of A—Q, $R^9OC(=O)OR^9$ or $R^{10}C(=O)OC(=O)R^{10}$ and 1–5 equivalents of bases are used for one equivalent of the thiadiazole derivative.

The thiadiazole derivatives represented by the formula [I] wherein A represents —$COOR^9$ or $CWNR^{11}R^{12}$ may be prepared as follows: That is, the thiadiazole derivative of the formula [XI] is reacted with phosgene, thiophosgene, trichloromethyl chloroformate or bis(trichloromethyl) carbonate in the presence or absence of a solvent in the presence or absence of a base at 0°–100° C. for several minutes to 48 hours.

Preferred examples of the solvent which may be used in this reaction may include aromatic hydrocarbons such as benzene and toluene; and halogenated hydrocarbons such as dichloromethane, chloroform and carbon tetrachloride.

Preferred examples of the base which may be used in this reaction may include organic bases such as pyridine, triethylamine and N,N-dimethylaniline; and inorganic bases such as sodium hydrogen carbonate and sodium carbonate.

Then the resultant is reacted with a corresponding alcohol or amine in the presence or absence of a solvent and in the presence or absence of a base at 0°–150° C. for several minutes to 48 hours, thereby the desired thiadiazole derivative may be obtained.

Preferred examples of the solvent which may be used in this reaction may include ketones such as acetone and methylethyl ketone, aromatic hydrocarbons such as benzene, toluene and xylene; ethers such as diethyl ether, tetrahydrofuran and dioxane, halogenated hydrocarbons such as dichloromethane, chloroform, dichloroethane and carbon tetrachloride; tertiary amines such as pyridine, triethylamine and N,N-dimethylaniline; polar solvents such as acetonitrile, N,N-dimethylformamide, acetonitrile, dimethylsulfoxide and 1,3-dimethyl-2-imidazolidinone.

Preferred examples of the base which may be used in this reaction may include organic bases such as pyridine and triethylamine; and inorganic bases such as sodium hydroxide, potassium carbonate and sodium hydrogen carbonate.

The thiadiazole derivatives represented by the formula [I] wherein A represents —$CWNR^{11}R^{12}$ may be prepared by reacting the thiadiazole derivative of the above-described formula [XI] with a corresponding isocyanate in the presence or absence of a solvent in the presence or absence of a base at 0°–150° C. for several minutes to 48 hours.

Preferred examples of the solvent which may be used in this reaction may include aromatic hydrocarbons such as benzene, toluene and xylene; ethers such as diethyl ether, tetrahydrofuran and dioxane; halogenated hydrocarbons such as dichloromethane, chloroform and carbon tetrachloride; and polar solvents such as pyridine, triethylamine, N,N-dimethylformamide, dimethylsulfoxide, 1,3-dimethyl-2-imidazolidinone and hexamethyl phosphoric triamide.

Preferred examples of the base which may be used in this reaction may include organic bases such as pyridine, triethylamine and N,N-dimethylaniline; inorganic bases such as sodium hydroxide, potassium hydroxide, sodium carbonate, potassium carbonate and sodium hydride.

The thiadiazole derivatives represented by the formula [I] wherein Y represents sulfur and A represents hydrogen may be prepared by thermally converting a corresponding thionocarbamate to the corresponding thiolcarbamate and by subsequent hydrolysis.

This reaction may be carried out under nitrogen atmosphere in the absence of a solvent at 130°–200° C. for several minutes to 24 hours, followed by the hydrolysis.

Further, in cases where at least one of X, V and Z in formula [I] is nitro, the thiadiazole derivative of the formula [I] may be prepared by reacting the thiadiazole derivative represented by the formula [XII] with conc. sulfuric acid/ conc. nitric acid at –10° C. to 100° C. for several minutes to 24 hours.

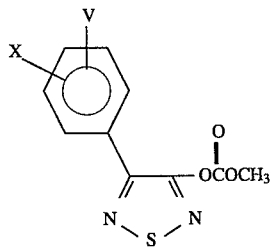

[XII]

(wherein X and V represent the same meaning as in formula [I]) Usually, 4 parts by weight of the thiadiazole derivative of the formula [XII] may be reacted with 10–100 parts by weight of conc. sulfuric acid and 1–100 parts by weight of conc. nitric acid.

In a second aspect of the present invention, thiadiazole derivatives represented by the above-described formula [II] are provided.

Among the groups designated by $R^{17}$ and $R^{18}$ in the formula [II], those preferred are $C_1$–$C_6$ linear or branched lower alkyl groups such as methyl, ethyl, propyl, butyl, pentyl and hexyl; $C_1-C_7$ cycloalkyl groups such as cyclopentyl, cyclohexyl and cyloheptyl; and alkoxyalkyl groups in which an alkyl group is substituted with $C_1-C_6$ linear or branched lower alkoxy group such as methoxyethyl, methoxypropyl, ethoxyethyl, ethoxypropyl, propoxyethyl, propoxypropyl and isopropoxypropyl. $R^{17}$ and $R^{18}$ may also cooperatively form a cyclic amine. Preferred examples of the cyclic amine may include pyrrolidine, piperidine, hexamethyleneamine, morpholine and piperazine which may be substituted with $C_1-C_4$ linear or branched lower alkyl.

$R^{17}$ and $R^{18}$ in the formula [II] most preferably represent lower alkyl, cycloalkyl or alkyleneamine.

The thiadiazole derivatives represented by the formula [II] may be prepared by reacting a corresponding amine, carbonyl sulfide and 3-chloromethyl-1,2,5-thiadiazole in a solvent in the presence or absence of a base according to the method described below (Japanese Laid Open Patent Application (Kokai) No. 73732/79).

The dithiol carbamates may also be prepared in the similar manner by reacting a corresponding amine, carbon disulfide and 3-chloromethyl-1,2,5-thiadiazole in a solvent in the presence or absence of a base.

These reactions may be carried out by reacting the above-described reactants in a solvent at 0°–100° C. for 1–24 hours.

Preferred examples of the solvent which may be employed in these reactions may include water; alcohols such as methanol and ethanol; aromatic hydrocarbons such as benzene and toluene; and pyridine. Among these, most preferred are water, ethanol, toluene and pyridine.

Preferred examples of the base which may be employed in these reactions may include organic bases such as pyridine, triethylamine and N,N-dimethylaniline, and inorganic bases such as sodium hydroxide, potassium hydroxide, sodium carbonate, potassium carbonate and sodium hydride. Among these, most preferred is sodium hydroxide.

The amount of the amine subjected to the reaction may be not less than 2 equivalents with respect to 1 equivalent of 3-chloromethyl-1,2,5-thiadiazole in the absence of the base, or not less than 1 equivalent with respect to 1 equivalent of 3-chloromethyl-1,2,5-thiadiazole in the presence of the base.

The amount of the base may be not less than 1 equivalent with respect to 1 equivalent of 3-chloromethyl-1,2,5-thiadiazole.

In a third aspect of the present invention, the thiadiazole derivatives represented by the above-described formula [III] are provided.

In the formula [III], $R^{23}$ represents phenyl group which is substituted with $C_1-C_6$ alkyl such as 2,6-dimethylphenyl, 2,6-diethylphenyl, 2-methyl-6-ethylphenyl, 2,6-dipropylphenyl, 2-methyl-6-propylphenyl and 2,4,6-trimethylphenyl; $C_1-C_8$ alkenyl such as 1-propenyl, 1-methyl-1-propenyl and 1,3-dimethylbutenyl; or cycloalkenyl which may be substituted with $C_1-C_6$ linear or branched alkyl such as 1-cyclohexyl, 1-cyclopentyl, 2,6-dimethyl-1-cyclohexynyl and 2,6-dimethyl-1-cyclopentenyl.

The thiadiazole derivative of the formula [III] may be prepared according to one of the following reactions [A] to [C].

Reaction [A]

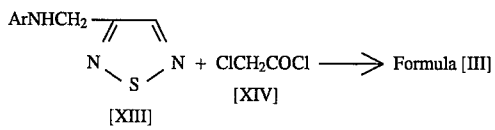

(wherein Ar represents phenyl group which is substituted with $C_1-C_6$ linear or branched alkyl)

Reaction [B]

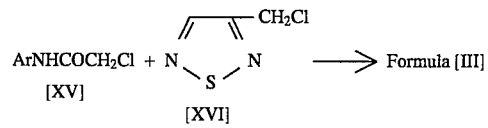

(wherein Ar represents the same meaning as in formula [XIII])

Reaction [C]

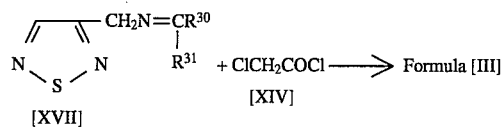

(wherein $R^{30}$ and $R^{31}$, the same or different, represent $C_1-C_6$ linear or branched alkyl or $R^{30}$ and $R^{31}$ cooperatively form $C_1-C_{18}$ alicyclic group).

In the Reaction [A], the amine represented by the formula [XIII] and chloroacetyl chloride represented by the formula [XIV] are reacted in the presence or absence of a solvent in the presence of a base at 0°–150° C. for several minutes to 48 hours.

The reaction may preferably be carried out in the presence of a solvent. Preferred examples of the solvent which may be employed in the reaction may include aliphatic hydrocarbons such as hexane, heptane, ligroin and petroleum ether; aromatic hydrocarbons such as benzene, toluene and xylene; ethers such as diethyl ether, diisopropyl ether, dioxane, tetrahydrofuran and diethyleneglycoldimethyl ether; ketones such as acetone, methylethyl ketone, methylisobutyl ketone and cyclohexanone; halogenated hydrocarbons such as dichloromethane, chloroform, carbon tetrachloride, dichloroethane, chlorobenzene and dichlorobenzene; esters such as ethyl acetate and butyl acetate; nitriles such as acetonitrile and isobutylonitrile; dimethylforamide; and dimethylsulfoxide.

Preferred examples of the base which may be used in Reaction [A] may include organic bases such as pyridine, triethylamine and N,N-diethylaniline; alkaline metal hydroxides such as sodium hydroxide and potassium hydroxide; and alkaline metal carbonates such as sodium carbonate and potassium carbonate.

In Reaction [A], 1–10 equivalents of the compound of the formula [XIV] and 1–10 equivalents of the base may usually be used per one equivalent of the compound of the formula [XIII].

The reaction [B] may be carried out by reacting the amide represented by the formula [XV] with 3-chloromethyl- 1,2, 5-thiadiazole of the formula [XVI] in a solvent in the presence of a base at 0°–150° C. for several minutes to 48 hours.

The reaction may preferably be carried out in a solvent. Preferred examples of the solvent may include aromatic hydrocarbons such as benzene, toluene and xylene; ethers such as diisopropyl ether, dioxane, tetrahydrofuran, diethyleneglycol dimethylether; ketones such as acetone, methylethyl ketone, methylisobutyl ketone and cyclohexanone; halogenated hydrocarbons such as dichloromethane, chloroform, carbon tetrachloride, dichloroethane, chlorobenzene and dichlorobenzene; esters such as ethyl acetate and butyl acetate; nitriles such as acetonitrile and isobutylonitrile; dimethylformamide; and dimethylsulfoxide.

Preferred examples of the base which may be used in Reaction [B] are the same as those preferred in Reaction [A].

In Reaction [B], 1–10 equivalents of the compound of the formula [XVI] and 1–10 equivalents of the base may usually be used per one equivalent of the compound the formula [XV].

The Reaction [C] may be carried out by reacting the amine of the formula [XVII] with chloroacetyl chloride of the formula [XIV] in the presence or absence of a solvent in the presence or absence of a base at 0°–150° C. for several minutes to 48 hours.

The Reaction [C] may preferably be carried out in a solvent in the absence of a base.

Preferred examples of the solvent which may be employed in Reaction [C] may include those preferred in Reaction [B].

Examples of the base which may be employed in Reaction [C] may include those preferred in Reaction [A].

In Reaction [C], 1–10 equivalents of the compound of the formula [XIV] and 1–10 equivalents of the base may usually be used per one equivalent of the compound of the formula [XVII].

In a fourth aspect of the present invention, a thiadiazole derivative of the above-described formula [IV] is provided.

In the formula [IV], $R^{24}$ and $R^{25}$, the same or different, represents hydrogen or halogen such as fluorine, chlorine, bromine and iodine; $R^{26}$ and $R^{27}$, the same or different, represents hydrogen, lower alkyl preferably $C_1$–$C_6$ linear or branched alkyl such as methyl, ethyl, n-propyl, isopropyl, n-butyl, isobutyl, sec-butyl, tert-butyl, n-pentyl, isopentyl, n-hexyl and isohexyl, or —$COR^{28}$ (wherein $R^{28}$ represents lower alkyl or amino group which may be substituted with lower alkyl), or $R^{26}$ and $R^{27}$ cooperatively form phthaloyl group.

Among the compounds represented by the formula [IV], those represented by the above-described formula [V] may be prepared by reacting the thiadiazole derivative of the above-described formula [VI] with the amine of the above-described formula [VII]. This reaction may be carried out in a solvent in the presence or absence of copper and/or cuprous chloride at 60°–150° C. for several minutes to 48 hours. In the formula [VII], preferred examples of the lower alkyl groups represented by $R^{28}$ and $R^{29}$ may be $C_1$–$C_6$ linear or branched alkyl such as methyl, ethyl, n-propyl, isopropyl, n-butyl, isobutyl, sec-butyl, tert-butyl, n-pentyl, isopentyl, n-hexyl and isohexyl.

Preferred examples of the solvent which may be employed in this reaction may include alcohols such as methanol and ethanol; polar solvents such as N,N-dimethylformamide, dimethylsulfoxide, 1,3-dimethyl-2-imidazolidinone and hexamethyl phosphoric triamide; and water.

In this reaction, 1–100 equivalents of the amine of the formula [VIII], 1–10 equivalents of copper and 1– 10 equivalents of cuprous chloride may be used per 1 equivalent of the thiadiazole derivative of the formula [XIII].

Among the thiadiazole derivatives represented by the formula [IV], those represented by the above-described formula [VIII] may be prepared by reacting the thiadiazole derivative of the above-described formula [VI] with potassium phthalimide. This reaction may be carried out in a solvent at 80°–150° C. for several minutes to 48 hours.

Preferred examples of the solvent which may be used in this reaction may include alcohols such as methanol and ethanol; polar solvents such as N,N-dimethylformamide, dimethylsulfoxide, 1,3-dimethyl-2-imidazolidinone and hexamethyl phosphoric triamide; and water.

In this reaction, 1–10 equivalents of potassium phthalimide may be used per one equivalent of the thiadiazole derivative of the formula [VI].

Among the thiadiazole derivatives represented by the formula [IV], those represented by the above-described formula [IX] may be prepared by hydrolyzing the thiadiazole derivative of the above-described formula [VIII]. This hydrolysis may be carried out by treating the thiadiazole derivative of the formula [VIII] with an acid such as hydrochloric acid and sulfuric acid or hydrazine in a solvent at 50°–100° C. for several minutes to 24 hours.

Preferred examples of the solvent which may be used in this reaction may include alcohols such as methanol and ethanol; and water.

In this reaction, 1–100 equivalents of the acid or hydrazine is used for one equivalent of the thiadiazole derivative of the formula [VIII].

Among the thiadiazole derivatives of the formula [IV], those wherein $R^{26}$ and $R^{27}$ represent —$COR^{28}$ may be prepared by reacting the thiadiazole derivative of the above-described formula [IX] with X'—$COR^{28}$ (wherein X' represents halogen and $R^{28}$ represents the same meaning as in formula [IV]). This reaction may be carried out in the presence of a base and a solvent at 40°–150° C. for several minutes to 24 hours.

Preferred examples of the solvent which may be employed in this reaction may include ketones such as acetone and methylethyl ketone; aromatic hydrocarbons such as benzene, toluene and xylene; ethers such as diethyl ether, tetrahydrofuran and dioxane; halogenated hydrocarbons such as dichloromethane, chloroform, carbon tetrachloride, dichloroethane and chlorobenzene; tertiary amines such as pyridine, triethylamine and N,N-dimethylaniline; and polar solvents such as acetonitrile, N,N-dimethylformamide, dimethylsulfoxide, 1,3-dimethyl-2-imidazolidinone and hexamethyl phosphoric triamide.

Preferred examples of the base which may be employed in this reaction may include organic bases such as pyridine, triethylamine and N,N-dimethylaniline; inorganic bases such as sodium hydroxide, potassium hydroxide, sodium carbonate, potassium carbonate and sodium hydride; and alkaline earth metal alkoxide such as sodium methoxide and sodium ethoxide.

In this reaction, 1–5 equivalents of X'—$COR^{28}$ and 1–10 equivalents of the base are used for one equivalent of thiadiazole derivative of the formula [IX].

In still another aspect of the present invention, a herbicide composition comprising the thiadiazole derivative of the present invention represented by the formula [I], [II], [III] or [IV] in an agriculturally acceptable carrier is provided.

The herbicide composition of the present invention has excellent herbicidal effectiveness while it does not substantially damage the useful crops. More particularly, the herbicide composition of the present invention can inhibit the growth of weeds in fields such as slender rush, purslane, cocklebur, coreopsis species, ragweed, common lambsquarters, pale smartweed, chickweed, shepherd's purse, chickweed, jimsonweed, morningglory, nightshade, honblt, plaintain, velvetleaf, woodsorrel, catchweed badstraw, buckwheat, fleabane, horseweed, daisy fleabane, barnyardgrass, green foxtail, large crabgrass, annual bluegrass, water foxtail, oats and johnsongrass, as well as the weeds in paddy fields such as barnyardgrass, falsepinpernel, spindle-flowered rotala, small flower umbrellaplant, bulrush, slender spikerush, water mutgrass, monochoria and arrowhead species. The herbicidal effect is exhibited either before the germination of the weeds or during the growth of the weeds. On the other hand, the herbicide composition of the present invention does not substantially damage the useful crops such as corn, wheat, rice, soybean, cotton and beat.

The herbicide composition of the present invention may contain other agricultural chemicals such as pesticides, fungicides, herbicides and plant growth regulators, as well as fertilizers and soil improvers. In particular, by blending one or more herbicides, the labor of application of the herbicides is reduced and the range of the weeds which can be controlled by the composition may be widen. Examples of such herbicides may include triazine-based herbicides such as 2,4-bis(ethylamino)- 6-ethylthio-1,3,5-triazine (common name: simetryne), 2,4-bis(isopropylamino)-6-methylthio-1,3,5-triazine (common name: prometryne) and 2-(1,2-dimethylpropylamino)- 4-ethylamino-6-methylthio-1,3,5-triazine (common name: dimethametryn); carbamate-based herbicides such as S-4-chlorobenzyl N,N-diethylthiocarbamate (common name: benthiocarb), S-α,α-dimethylbenzyl N,N-pentamethylenethio carbamate (common name: dimepiperate), S-benzyl N-ethyl-N-(1,2-dimethylpropyl)thiocarbamate (common name: esprocarb), S-ethylhexahydro-1H-azepine-1-carbothioate (common name: molinate), and O-3-tert-butylphenyl N-(6-methoxy-2-pyridyl)-N-methylthiocarbamate (common name: piributycarb); phenoxy-based herbicides such as 2,4-D, MCPB, 2-(2-naphthyloxy)propionanilide (common name: naproanilide), and 2-(2,4-dichloro-3-methylphenoxy)propionanilide (common name: clomeprop); diphenyl ether-based herbicides such as 2,4,6-trichlorophenyl 4-nitrophenyl ether (common name: chloronitrofen), 2,4-dichlorophenyl 3-methoxy-4-nitrophenyl ether (common name: chloromethoxynil), 2,4-dichlorophenyl 3-methoxycarbonyl-4-nitrophenyl ether (common name: bifenox) and 2-chloro-4-trifluoromethylphenyl 4-nitro-3-(tetrahydropyrane-3-yloxy)phenyl ether (test code: MT-124); amide-based herbicides such as N-butoxymethyl-2-chloro-2',6'-diethylacetoanilide (common name: butachlor), N-propoxyethyl-2-chloro2',6'-diethylacetoanilide (common name: pretilachlor), N-methyl-2-(2-benzothiazolyloxy)acetoanilide (common name: mefenacet), 2',3'-dichloro-4-ethoxymathoxybenzanilide (test code: HW-52), N-(α,α-dimethylbenzyl)-2-bromo-3,3-dimethylbutylamide (common name: bromobutide), and 3',4'-dichloropropionanilide (common name: propanil); urea-based herbicides such as 1-(α,α-dimethylbenzyl)-3-(4-methylphenyl)urea (common name: dymron) and 1-(2-chlorobenzyl)-3-(α,α-dimethylbenzyl)urea (test code: JC-940); quinone-based herbicides such as 2-amino-3-chloro-1,4-naphthoquinone (common name: ACN); heterocycle-based herbicides such as 4-(2,4-dichlorobenzoyl)-1,3-dimethyl-5-pyrazolyl p-toluenesulfonate (common name: pyrazolate), 4-(2,4-dichlorobenzoyl)- 1,3-dimethyl-5-phenasyloxypyrazole (common name: pyrazoxyfen), 4-(2,4-dichloro-3-methylbenzoyl)- 1,3-dimethyl-5-(4-methylphenasyloxy)pyrazole (common name: benzofenap), 5-benzyloxy- 4-(2,4-dichlorobenzoyl)-1-methylpyrazole (test name: NC-310), 5-tert-butyl-3-(2,4-dichloro-5-isopropoxyphenyl)- 1,3,4-oxadiazole-2-(3H)-one (common name: oxadiazone), 3,7-dichloro-8-quinoline carboxylic acid (common name: quinolorac), 3-chloro-2-[2-fluoro-4-chloro-5-(1-propynyloxy)phenyl]-4,5,6,7-tetrahydro-2H-imidazole (test code: S-275), 3-isopropyl-2,1,3-benzothiaziadinone-4)-2,2-dioxide (common name: bentazone), and 1-(3-methylphenyl)-5-phenyl-1H-1,2,4-triazole- 3-carboxamide (test code: KNW-242); organic phosphur-based herbicides such as O,O-diisopropyl-2-(benzenesulfonamide)ethylenedithiophosphate (common code: SAP); and sulfonylurea-based herbicides such as methyl 2-[[[[(4,6-dimethoxypyrimidine-2-yl)amino]carbonyl] amino]sulfonyl]methyl] benzoate (common name: londax) and ethyl 5-[3-(4,6-dimethoxypyrimidine-2-yl)ureidosulfonyl]-1-methylpirazole-4-carboxylate (common name: pyrazosulfuron ethyl).

The herbicide composition of the present invention may be in the form of an emulsifiable concentrate, wettable powder, flowable powder, granules or powder. These formulations may be prepared by formulating the effective ingredient of the present invention with an agriculturally acceptable carrier such as a solid carrier, solvent, surfactant and a formulation aid.

Examples of the solid carrier include kaolin, clay, bentonite, diatomaceous earth, acidic terra abla, white carbon and pumice powder. Examples of the solvent include aromatic hydrocarbons such as xylene and methylnaphthalene, alcohols such as isopropanol, ethyleneglycol and cellosolve; ketones such as acetone and cyclohexanone; mineral oil; dimethylsulfoxide; N,N-dimethylformamide; acetonitrile and water. Examples of the surfactants include anion surfactants such as salts of alkyl sulfate, alkyl sulfonate and aryl sulfonate; and non-ion surfactants such as polyoxyethyleneglycol ethers, polyoxyethyleneglycol esters and polyol esters. Examples of other formulation aids include polyvinyl alcohol, lignin sulfonate and acacia.

The herbicide composition of the present invention usually contains 0.1–90% by weight, preferably 1–80% by weight of the effective ingredient of the present invention.

The amount of the compound of the present invention to be applied to the field varies depending on the weather conditions, formulation of the composition, timing of application, method of application, field conditions, species and stage of growth of the weeds and on the crops. Usually, the amount to be applied may be 1– 1000 g/10 a, preferably 2–500 g/10 a in terms of the weight of the effective ingredient of the present invention.

The herbicide composition of the present invention may directly be applied to the leaves or stems of weeds or to the field before the germination of the weeds.

The invention will now be described by way of examples thereof. The examples are presented for the illustration purpose only and should not be interpreted in any restrictive way.

EXAMPLE 1

Preparation of 3-(2,6-dichlorophenyl)-4-hydroxy-1,2,5-thiadiazole (Compound No. 11 (see Table 1))

In N,N-dimethylformamide, 14.5 g of 2,6-dichlorophenyl glycine amide hydrobromic acid salt was dissolved and 19.5 g of sulfur monochloride was added thereto. The mixture was stirred for 12 hours at room temperature. The mixture was then poured into water and was converted to alkaline with sodium hydroxide, followed by removal of insoluble materials by filtration. The filtrate was converted to acidic with hydrochloric acid and the generated precipitates were extracted with ether. The ether layer was washed twice with dilute hydrochloric acid and then twice with saturated sodium chloride solution, followed by drying over anhydrous sodium sulfate. The solvent was evaporated off and the obtained crystals were recrystallized from chloroform to obtain 9.5 g of 3-(2,6-dichlorophenyl)-4-hydroxy-1,2,5-thiadiazole.

m.p.: 194°–195° C.

$^1$H-NMR (CDCl$_3$, δ ppm) 7.3–7.6 (m).

IR (KBr, cm$^{-1}$) 3200–2400, 1540, 1505, 1435, 1230, 880, 790, 775.

Elemental analysis for C$_8$H$_4$N$_2$OSCl$_2$; Calcd.: C;38.88, H;1.63, N;11.33; Found: C;39.00, H;1.48, N;11.53.

EXAMPLE 2

Preparation of 4-(2,6-dichlorophenyl)-1,2,5-thiadiazol-3-yl N,N-dimethyl carbamate (Compound No. 7)

In acetonitrile, 0.25 g of 3-(2,6-dichlorophenyl)-4-hydroxy-1,2,5-thiadiazole and 0.15 g of potassium carbonate were suspended and 0.12 g of dimethylcarbamoyl chloride was added thereto. The mixture was heated to reflux for 12 hours. After allowing to cool, the mixture was poured into water and extracted with ether. The ether layer was washed twice with dilute sodium hydroxide solution, twice with water and twice with aqueous saturated sodium chloride solution. The extract was dried over anhydrous sodium sulfate and the resultant was condensed, followed by silica gel column chromatography to obtain 0.25 g of 4-(2,6-dichlorophenyl)-1,2,5-thiadiazol-3-yl N,N-dimethyl carbamate.

m.p.: 115°–116° C.

$^1$H-NMR (CDCl$_3$, δppm) 2.87 (s, 3H), 2.93 (s, 3H), 7.2–7.45 (m, 3H).

IR (KBr, cm$^{-1}$) 1735, 1365, 1235, 1150, 785.

Elemental analysis for C$_{11}$H$_9$N$_3$OSCl$_2$; Calcd.: C;41.52, H;2.85, N;13.20; Found: C;41.58, H;2.86, N;13.04.

EXAMPLE 3

Preparation of 4-(2,6-dichlorophenyl)-1,2,5-thiadiazol-3-yl acetate (Compound No. 66)

In ether, 0.5 g of 3-(2,6-dichlorophenyl)-4-hydroxy-1,2,5-thiadiazole and 0.18 g of pyridine were dissolved and 0.23 g of acetic anhydride was added thereto. The mixture was stirred for 3 hours at room temperature. The reaction mixture was poured into water and extracted with ether. The ether layer was washed twice with aqueous dilute sodium hydroxide solution, twice with water and twice with aqueous saturated sodium chloride solution. The resultant was dried over anhydrous sodium sulfate and concentrated, followed by silica gel column chromatography to obtain 0.41 g of 4-(2,6-dichlorophenyl)-1,2,5-thiadiazol-3-yl acetate.

m.p.:.56°–59° C.

$^1$H-NMR (CDCl$_3$, δppm) 2.17 (s, 3H), 7.15–7.4 (m, 3H)

IR (KBr, cm$^{-1}$) 1795, 1430, 1175, 780.

Elemental analysis for C$_{10}$H$_6$N$_2$O$_2$SCl$_2$; Calcd.: C;41.54, H;2.09, N;9.68; Found: C;41.23, H;2.27, N;9.84.

EXAMPLE 4

Preparation of 4-(2,6-dichlorophenyl)-1,2,5-thiadiazol-3-yl N-(3-methoxypropyl)-N-methyl carbamate (Compound No. 62)

In benzene, 0.49 g of 3-(2,6-dichlorophenyl)-4-hydroxy-1,2,5-thiadiazole and 0.21 g of bis(trichloromethyl)carbonate were dissolved. To the mixture, 0.2 g of pyridine was added and the mixture was stirred at room temperature for 12 hours. Then 0.41 g of N-methyl-N-(3-methoxypropyl)amine was added to the mixture and the resulting mixture was stirred at room temperature for 12 hours. The reaction mixture was poured into water and was extracted with ether. The ether layer was washed three times with dilute aqueous sodium hydroxide solution, three times with dilute hydrochloric acid, twice with water and then twice with aqueous saturated sodium chloride solution. The resultant was dried over anhydrous sodium sulfate and condensed, followed by silica gel column chromatography to obtain 0.38 g of 4-(2,6-dichlorophenyl)-1,2,5-thiadiazol- 3-yl N-(3-methoxypropyl)-N-methyl carbamate.

$n_D^{25.0}$: 1.5638

$^1$H-NMR (CDCl$_3$, δppm): 1.4–2.0 (m, 2H), 2.92 (broad s, 3H), 3.1–3.6 (m, 7H), 7.25–7.5 (m, 3H).

IR (NaCl, cm$^{-1}$) 1745, 1430, 1385, 1230, 1120, 790.

Elemental analysis for C$_{14}$H$_{15}$N$_3$O$_3$SCl$_2$; Calcd.: C;44.69, H;4.01, N;11.16; Found: C;44.34, H;4.05, N;10.92.

EXAMPLE 5

Preparation of 4-(2,6-dichlorophenyl)-1,2,5-thiadiazol-3-yl N,N-dimethylthiol carbamate (Compound No. 35)

Under nitrogen atmosphere, 1.34 g of 4-(2,6-dichlorophenyl)- 1,2,5-thiadiazol-3-yl N,N-dimethylthiono carbamate was heated to 180° C. After allowing to cool, the reaction mixture was purified by silica gel column chromatography to obtain 0.8 g of 4-(2,6-dichlorophenyl)-1,2,5-thiadiazol-3-yl N,N-dimethylthiol carbamate m.p.: 168°–170° C.

$^1$H-NMR (CDCl$_3$, δppm) 2.93 (s, 6H), 7.2–7.45 (m, 3H).

IR (KBr, cm$^{-1}$) 1690, 1430, 1090, 785.

Elemental analysis for C$_{11}$H$_9$N$_3$OS$_2$Cl$_2$; Calcd.: C;39.52, H;2.71, N;12.57; Found: C;39.38, H;2.83, N;12.79.

EXAMPLE 6

Preparation of 3-(2,6-dichlorophenyl)-4-mercapto-1,2,5-thiadiazole (Compound No. 38)

To a mixed solvent of 15 ml of ethanol and 0.3 ml of water, 0.6 g of 4-(2,6-dichlorophenyl)-1,2,5-thiadiazol-3-yl N,N-dimethylthiol carbamate and 0.28 g of potassium hydroxide were added and the mixture was heated to reflux for 15 hours. Ethanol was removed from the reaction mixture and aqueous dilute sodium hydroxide solution was added to the resulting mixture, followed by extraction with ether. The aqueous layer was extracted with ether after converting it to acidic with hydrochloric acid. The ether layers were washed twice with dilute hydrochloric acid and twice with saturated aqueous sodium chloride solution, and the resultant was dried over anhydrous sodium sulfate, followed by removal of the solvent to obtain 0.4 g of 3-(2,6-dichlorophenyl)-4-mercapto-1,2,5-thiadiazole.

m.p.: 91°–94° C.

$^1$H-NMR (CDCl$_3$, δppm) 3.09 (broad s, 1H), 7.53 (s, 3H).

IR (KBr, cm$^{-1}$) 2550, 1430, 1345, 1175, 820, 790, 785.

Elemental analysis for C$_8$H$_4$N$_2$S$_2$Cl$_2$; Calcd.: C;36.51, H;1.53, N;10.64; Found: C;36.82, H;1.38, N;10.58.

EXAMPLE 7

Preparation of 4-(2,6-dichlorophenyl)-1,2,5-thiadiazol-3-yl N-methyl carbamate (Compound No. 75)

In pyridine, 0.25 g of 3-(2,6-dichlorophenyl)-4-hydroxy-1,2,5-thiadiazole was dissolved and 0.17 g of methyl isocyanate was added to the solution. The mixture was stirred at room temperature for 19 hours. The reaction mixture was then poured into water and extracted with ether. The ether layer was washed twice with dilute hydrochloric acid and twice with saturated aqueous sodium chloride solution, and the resultant was dried over anhydrous sodium sulfate. The resultant was condensed and purified by silica gel chromatography to obtain 0.24 g of 4-(2,6-dichlorophenyl)-1,2,5-thiadiazol-3-yl N-methyl carbamate.

m.p.: 118°–122° C.

$^1$H-NMR (CDCl$_3$, δppm) 2.75 (d, J=5Hz, 3H), 5.3 (broad s, 1H), 7.2–7.5 (m 3H).

IR (KBr, cm$^{-1}$) 3290, 1760, 1730, 1400, 1225.

Elemental analysis for C$_{10}$H$_7$N$_3$O$_2$SCl$_2$; Calcd.: C;39.49, H;2.31, N;13.81; Found: C;39.66, H;2.48, N;14.13.

In the similar manner, various compounds represented by the formula [I] were prepared. The structures thereof as well as the physical properties are shown in Table 1.

EXAMPLE 8

Preparation of 4-(2,6-dichloro-3-nitrophenyl)-3-yl methyl carbonate (Compound No. 104)

To mixed acid (mixture of 9 ml of concentrated sulfuric acid and 9 ml of concentrated nitric acid), 2.75 g of 3-(2,6-dichlorophenyl)-4-hydroxy-1,2,5-thiadiazole was added and the resulting mixture was stirred for 4 hours at room temperature. The resulting reactin mixture was poured into water and the resultant was extracted with ether. The ether layer was washed twice with water and twice with saturated aqueous sodium chloride solution. The resultant was dried over anhydrous sodium sulfate and the solvent was distilled off to obtain 3.15 g of 4-(2,6-dichloro-3-nitrophenyl)-3-yl methyl carbonate.

Viscose Oil $^1$H-NMR (solvent: CDCl$_3$, δppm) 3.93 (s,3H), 7.62(d,J=8.5Hz,1H), 7.59(d,J=8.5Hz, 1H).

IR (NaCl, cm$^-$): 1785, 1540, 1530, 1250, 1220.

Elementary Analysis (%): Calcd.: C; 34.30, H;1.43, N;12.00; Found: C;34.30, H:1.56, N;11.97.

In the similar manner, various compounds represented by the formula [I] were prepared. The structures thereof as well as the physical properties are shown in Table.

EXAMPLE 9

Preparation of Wettable Powder

Ten parts of the compound of the present invention, 86.5 parts by weight of Zeaklite (commercially available from Zeaklite Kagaku Kogyo), 2 parts by weight of New Cargen NV-406 (commercially available from Takemoto Oil) and 1.5 parts by weight of Disksol WA (commercially available from Daiichi Kogyo Seiyaku) were mixed and the mixture was pulverized to obtain wettable powder.

EXAMPLE 10

Preparation of Emulsifiable Concentrate

Five parts by weight of the compound of the present invention, 75 parts by weight of xylene and 20 parts by weight of Solpol 2806B (a surfactant commercially available from Toho Kagaku Kogyo) were mixed and the mixture was uniformly stirred to obtain emulsifiable concentrate.

EXAMPLE 11

Preparation of Granules

Ten parts by weight of the compound of the present invention, 50 parts by weight of bentonite, 35 parts by weight of Kunilite (commercially available from Kunimine Kogyo) and 5 parts by weight of Solpol 800A (a surfactant commercially available from Toho Kagaku Kogyo) were mixed and the mixture was pulverized. Water was added to the resulting mixture and the mixture was stirred. The mixture was then formed into granules and dried to obtain granules.

EXAMPLE 12

Test for Evaluation of Effectiveness in Growth Inhibition 10 of Weeds by Treatment of Water in Paddy Field In a plastic pot of 100 cm$^2$, plowed soil of paddy field was packed and the seeds of weeds shown in Table 2 were sown. Two two-leaves stage seedlings of paddy rice were planted per 1 pot and the soil was covered with water of 2 cm thickness. In the germination period of the weeds, the herbicide composition in the form of wettable powder formulated as in Example 9 was dropped on the water in the amount shown in Table 2. The pots were placed in a green house and water was appropriately supplied to the pots. After 20 days from the treatment with the herbicide, the herbicidal effectiveness and damage of the rice were examined. The results are shown in Table 2. The herbicide effectiveness as well as the damage of the crops is classified into 6 ranks according to the following criteria:

| Herbicidal Effectiveness | Rate of Growth Inhibition |
| --- | --- |
| 0 | 0–9% |
| 1 | 10–29% |
| 2 | 30–49% |
| 3 | 50–69% |
| 4 | 70–89% |
| 5 | 90–100% |

EXAMPLE 13

Preparation of S-3-1,2,5-thiadiazolyl methyl N,N-diethylthiol carbamate (Compound No. 131)

In a 50 ml pear-shaped flask, 1.08 g of diethylamine and 1.08 g of water were placed and 0.89 g of carbonyl sulfide was bubbled at 15°–20° C. with stirring and cooling with water. To the mixture, 1 g of 3-chloromethyl- 1.2.5-thiadiazole was added dropwise. After completion of the addition, the mixture was heated at 50° C. for 3 hours under stirring. After allowing to cool, the mixture was extracted with ether. The organic layer was washed with 1N hydrochloric acid and water, and the resultant was dried over anhydrous magnesium sulfate. The solvent was evaporated under reduced pressure and the residue was distilled to obtain 1.05 g of S-3-1,2,5-thiadiazolyl methyl N,N-diethylthiol carbamate (Compound No. 131).

b.p.: 106° C./0.5 mmHg $^1$H-NMR (CDCl$_3$, δppm) 1.0 (6H, t, d=7Hz), 3.28 (4H, q, J=7Hz), 4.30 (2H,s), 8.5 (1H, s).

IR (NaCl, cm$^{-1}$) 1650.

Elemental analysis for C$_8$H$_{13}$N$_3$OS$_2$; Calcd.: C;41.53, H;5.66, N;18.16; Found: C;41.10, H;5.46, N;17.99.

EXAMPLE 14

Preparation of S-3-1,2,5-thiadiazolylmethyl N,N-dimethylthiol carbamate (Compound No. 132)

To a solution composed of 1.34 g of dimethylamine and 1.34 g of water, carbonyl sulfide was bubbled to saturation under cooling with water, and 1 g of 3-chloromethyl-1,2,5-thiadiazole was added dropwise thereto. Thereafter, the procedure in Example 13 was followed to obtain 0.73 g of S-3-1,2,5-thiadiazolylmethyl N,N-dimethylthiol carbamate (Compound No. 132).

b.p.: 99° C./0.4 mmHg $^1$H-NMR (CCl$_4$, δppm) 2.95 (6H, s), 4.32 (2H, s), 8.5(1H, s).

IR (NaCl, cm$^{-1}$) 1650.

Elemental analysis for C$_6$H$_9$N$_3$OS$_2$; Calcd.: C;35.45, H;4.46, N;20.78; Found: C;35.78, H;4.47, N;20.78.

EXAMPLE 15

Preparation of S-3-1,2,5-thiadiazolylmethyl N,N-diisopropylthiol carbamate (Compound No. 133)

To a solution composed of 1.50 g of diisopropylamine and 1.5 g of water, carbonyl sulfide was bubbled to saturation and then 1 g of 3-chloromethyl-1,2,5-thiadiazole was dropped into the mixture. The mixture was heated at 50° C. for 3 hours under stirring. After allowing to cool, the mixture was extracted with ether. The organic layer was washed with 1N hydrochloric acid and water, and the resultant was dried over anhydrous magnesium sulfate. The solvent was evaporated under reduced pressure and the residue was purified by silica gel column chromatography (eluant: benzene/ethyl acetate= 10/1) to obtain 1.09 g of S-3-1,2,5-thiadiazolylmethyl N,N-diisopropylthiol carbamate (Compound No. 133).

Refractive Index: n$_D^{25}$=1.5470

$^1$H-NMR (CCl$_4$, δppm) 1.32 (6H, d, J=7Hz), 3.4–4.2 (2H, m), 4.38 (2H, s), 8.50 (1H, s).

IR (NaCl, cm$^{-1}$) 1635.

Elemental analysis for C$_{10}$H$_{17}$N$_3$OS$_2$; Calcd.: C;46.30, H;6.60, N;16.19; Found: C;46.40, H;6.69, N;16.29.

EXAMPLE 16

Preparation of S-3-1,2,5-thiadiazolyl N,N-dimethyldithio carbamate (Compound No. 136)

To 1 ml of aqueous solution containing 0.67 g of dimethylamine, 0.57 g of carbon disulfide was added dropwise under cooling in ice. After stirring in ice for 30 minutes, 1 g of 3-chloromethyl-1,2,5-thiadiazole was added to the mixture. Thereafter, the procedure in Example 15 was followed to obtain 1.28 g of S-3-1,2,5-thiadiazolyl N,N-dimethyldithio carbamate (Compound No. 136).

Refractive Index: n$_D^{25}$=1.6508.

$^1$H-NMR (CCl$_4$, δppm) 3.40 (6H, s), 4.75 (2H, s), 8.52 (1H, s).

Elemental analysis for C$_6$H$_9$N$_3$OS$_2$; Calcd.: C;32.85, H;4.13, N;19.15; Found: C;32.48, H;4.04, N;19.03.

In the similar manner, various compounds represented by the formula [II] were prepared. The structures thereof as well as the physical properties are shown in Table 3.

EXAMPLE 17

Test for Evaluation of Effectiveness in Growth Inhibition of Weeds by Treatment of Water in Paddy Field The compounds shown in Table 4 formulated into wettable powder according to Example 9 were tested for their effectiveness in growth inhibition of weeds in the same manner as in Example 12. The results are shown in Table 4.

EXAMPLE 18

Preparation of N-(1,2,5-thiadiazolyl-3-methyl)-N-(2,6-diethylphenyl)-α-chloroacetamide (Compound No. 178)

To a 100 ml three-necked flask, 30 ml of anhydrous dimethylsulfoxide, 0.7 g of pulverized potassium hydroxide powder and 2 g of N-2,6-diethylphenyl-α-chloroacetamide were placed. Under nitrogen atmosphere, the mixture was stirred at room temperature until the mixture became a uniform solution. To the thus obtained uniform solution, 1.2 g of 3-chloromethyl-1,2,5-thiadiazole was added under cooling in ice. After the addition, the mixture was stirred at room temperature for one hour and 30 ml of iced water was added to the reaction mixture. The resulting mixture was then extracted with ether and the organic layer was dried over anhydrous magnesium sulfate, followed by evaporation of the solvent. The residue was purified by silica gel column chromatography to obtain 0.55 g of the desired product.

m.p.: 77.5°–78° C.

IR (KBr, cm$^{-1}$) 1650.

$^1$H-NMR (CDCl$_3$, δppm) 1.08 (6H, d, J=7Hz), 2.22 (4H, q, J=7Hz), 3.68 (2H, s), 5.00 (2H, s), 6.95–7.32 (3H, m), 8.77 (1H, s).

EXAMPLE 19

Preparation of N-(1,2,5-thiadiazolyl-3-methyl)-N-(2,6-dimethylphenyl)-α-chloroacetamide (Compound No. 179)

The same procedure as in Example 18 was repeated except that 30 ml of dimethylsulfoxide, 0.5 g of potassium hydroxide and 1.58 g of N-(2,6-dimethylphenyl)-α-chloroacetamide were used to obtain 0.9 g of the desired product.

m.p.: 75°–76° C.

IR (KBr, cm$^{-1}$) 1650.

$^1$H-NMR (CDCl$_3$, δppm) 1.65 (6H, s), 3.70 (2H, s), 5.02 (2H, s), 7.0–7.3 (3H, m), 8.76 (1H, s).

EXAMPLE 20

Preparation of
N-(1,2,5-thiadiazolyl-3-methyl)-N-(2-methyl-6-ethylphenyl)-α-chloroacetamide (Compound No. 180)

The same procedure as in Example 18 was repeated except that 10 ml of dimethylsulfoxide, 20 ml of tetrahydrofuran, 0.5 g of potassium hydroxide and 1.47 g of N-2,6-diethylphenyl-α-chloroacetamide were used to obtain 0.49 g of the desired product.

m.p.: 66°–67° C.

IR (KBr, cm$^{-1}$) 1650.

$^1$H-NMR (CDCl$_3$, δppm) 1.05 (3H, t, J=7Hz), 1.92 (3H, s), 2.27 (2H, q, J=7Hz), 3.80 (2H, s), 5.00 (2H, s), 6.82–7.44 (3H, m), 8.72 (2H, s).

EXAMPLE 21

Preparation of
N-(1,2,5-thiadiazolyl-3-methyl)-N-(2,6-dimethyl-1-cyclohexenyl)-α-chloroacetamide (Compound No. 181)

To 10 ml of a solution in toluene containing 0.7 g of 3-(N-2,6-dimethylcyclohexylideneaminomethyl)-1,2,5-thiadiazole obtained by the condensation of 2,6-dimethylcyclohexanone and 3-aminomethyl 1,2,5-thiadiazole, 0.4 g of chloro-α-chloroacetyl was added and the resulting mixture was stirred for 8 hours under heat. After allowing the mixture to cool, the solvent was evaporated under reduced pressure and the residue was purified by silica gel column chromatography to obtain 0.48 g of the desired product in the form of oil.

Refractive Index: n$_D^{25}$=1.5489

IR (NaCl, cm$^{-1}$) 1665.

$^1$H-NMR (CDCl$_3$, δppm) 0.72–2.75 (13H, m), 3.92 (2H, s), 4.71, 4.87 (2H, s), 8.65 (1H, s).

EXAMPLE 22

Preparation of N-(2-(4-methyl-2-butenyl))-N-(3-(1,2,5-thiadiazolyl)methyl)-α-chloroacetamide (Compound No. 182)

The same procedure as in Example 21 was repeated except that 1 g of a condensate of methylisopropyl ketone and 3-aminomethyl-1,2,5-thiadiazole, and 0.68 g of chloro-α-chloroacetyl was used to obtain 0.9 g of the desired product in the form of oil.

Refractive Index: n$_D^{25}$=1.5263.

IR (NaCl, cm$^{-1}$) 1665.

$^1$H-NMR (CDCl$_3$, δppm) 0.95 (6H, d, J=6.2Hz), 1.89 (3H, s), 2.08–2.82 (1H, m), 4.08 (2H, s), 4.82 (2H, s), 5.11 (1H, s), 8.55 (1H, s).

EXAMPLE 23

Test for Evaluation of Effectiveness in Growth Inhibition of Weeds by Treatment of Water in Paddy Field The compounds of Compound Nos. 178–182 formulated into wettable powder according to Example 9 were tested for their effectiveness in growth inhibition of weeds in the same manner as in Example 12. The results are shown in Table 5.

EXAMPLE 24

Preparation of
3-amino-4-(2,6-dichlorophenyl)-1,2,5-thiadiazole (Compound No. 183)

A solution in methanol containing 5.31 g of 3-chloro-4-(2,6-dichlorophenyl)-1,2,5-thiadiazole, 1.91 g of copper powder and 1.97 g of cuprous chloride saturated with ammonia gas was placed in a stainless steel vessel. After sealing the vessel, the solution was stirred at 120° C. for 24 hours. After allowing the mixture to cool, insoluble materials were removed by filtration. The filtrate was concentrated and the residue was purified by silica gel column chromatography to obtain 2.19 g of 3-amino- 4-(2,6-dichlorophenyl)-1,2,5-thiadiazole.

m.p.: 95°–97° C.

$^1$H-NMR (CDCl$_3$, δppm) 4.52 (s, 2H), 7.2–7.5 (m, 3H).

IR (KBr, cm$^{-1}$) 3425, 3325, 3210, 1620, 1535, 1490, 1430, 1420, 790, 780.

MS (m/z): 245 (M$^+$)

EXAMPLE 25

Preparation of
3-(4-chlorophenyl)-4-phthalimide-1,2,5-thiadiazole

To a solution of 1.16 g of 3-chloro-4-(4-chlorophenyl)-1,2,5-thiadiazole in N,N-dimethylformamide, 1.11 g of potassium phthalimide was added and the mixture was heated to reflux at 110° C. for 12 hours. After allowing to cool, the mixture was poured into water and the resultant was extracted with ether. The ether layer was washed twice with dilute aqueous sodium hydroxide solution, twice with water, and twice with saturated aqueous sodium chloride solution. The resultant was then dried over anhydrous sodium sulfate and concentrated. The residue was purified by silica gel column chromatography to obtain 0.85 g of 3-(4-chlorophenyl)-4-phthalimide- 1,2,5-thiadiazole.

m.p.: 152°–153° C.

$^1$H-NMR (CDCl$_3$, δppm) 7.1–7.4 (m, 2H), 7.4–7.7 (m, 2H), 7.7–8.0 (m, 4H).

IR (KBr, cm$^{-1}$) 1790, 1725, 1440, 1180, 885, 715.

MS (m/z): 341 (M$^+$).

EXAMPLE 26

Preparation of
3-amino-4-(4-chlorophenyl)-1,2,5-thiadiazole

To a solution of 0.41 g of 3-(4-chlorophenyl)-4-phthalimide- 1,2,5-thiadiazole in ethanol, 0.05 g of 80% aqueous hydrazine solution was added and the mixture was heated to reflux for one hour. After allowing to cool, the mixture was poured into water and extracted with ether. The ether layer was washed twice with water and twice with saturated aqueous sodium chloride solution. The resultant was dried over anhydrous sodium sulfate and the resultant was concentrated, followed by purification by silica gel column chromatography to obtain 0.21 g of 3-amino-4-(4-chlorophenyl)-1,2,5-thiadiazole.

m.p.: 132°–133° C.

$^1$H-NMR (acetone-d$_6$, δppm) 5.40 (bs, 2H), 7.2–7.5 (m, 2H), 7.5–7.8 (m, 2H).

IR (KBr, cm$^{-1}$) 3410, 3310, 3190, 1620, 1515, 1495, 1435, 1400, 1090, 830.

MS (m/z): 211 (M$^+$).

EXAMPLE 27

Preparation of 3-(2,6-dichlorophenyl)-4-methylamino-1,2,5-thiadiazole (Compound No. 184)

In a stainless steel vessel, 5.31 g of 3-chloro-4-(2,6-dichlorophenyl)-1,2,5-thiadiazole and 100 ml of 40% aqueous methylamine solution were placed. After sealing the vessel, the solution was stirred at 120° C. for 12 hours. After allowing to cool, the mixture was poured into water and was extracted with ether. The ether layer was washed three times with water and three times with saturated aqueous sodium chloride solution. The resultant was then dried over anhydrous sodium sulfate and then the resultant was concentrated, followed by purification by silica gel column chromatography to obtain 2.55 g of 3-(2,6-dichlorophenyl)-4-methylamino-1,2,5-thiadiazole.

m.p.: 145°–146° C.

$^1$H-NMR (CDCl$_3$, δppm) 3.02 (s, 3H), 4.10 (bs, 1H), 7.15–7.4 (m, 3H).

IR (KBr, cm$^{-1}$) 3320, 1555, 1425, 790, 775.

MS (m/z): 259 (M$^+$).

EXAMPLE 28

Preparation of 3-acetylamino-4-(2,6-dichlorophenyl)-1,2,5-thiadiazole (Compound No. 185)

To a solution containing 0.49 g of 3-amino-4-(2,6-dichlorophenyl)-1,2,5-thiadiazole and 0.22 g of triethylamine in N,N-diemthylformamide, 0.20 g of acetyl chloride was added and the mixture was stirred at 60° C. for 12 hours. After allowing to cool, the mixture was poured into water and was extracted with ether. The ether layer was washed twice with dilute hydrochloric acid, twice with water and twice with saturated aqueous sodium chloride solution. The resultant was dried over anhydrous sodium sulfate, concentrated and purified by silica gel chromatography to obtain 0.25 g of 3-acetylamino-4-(2,6-dichlorophenyl)-1,2,5-thiadiazole.

m.p.: 180°–185° C.

$^1$H-NMR (CDCl$_3$, δppm) 2.1 (s, 3H), 7.37 (s, 3H), 9.47 (bs, 1H).

IR (KBr, cm$^{-1}$) 3290, 1695, 1540, 1500, 1425, 1230, 785.

MS (m/z): 287 (M$^+$).

EXAMPLE 29

Preparation of 3-(2,6-dichlorophenyl)-4-phthalimide-1,2,5-thiadiazole (Compound No. 186)

To a solution of 2.66 g of 3-chloro-4-(2,6-dichlorophenyl)-1,2,5-thiadiazole in N,N-dimethylformamide, 2.22 g of potassium phthalimide was added and the mixture was heated to reflux at 110° C. for 12 hours. After allowing to cool, the mixture was poured into water and was extracted with ether. The ether layer was washed twice with dilute aqueous sodium hydroxide solution, twice with water and twice with saturated aqueous sodium chloride solution. The resultant was dried over anhydrous sodium sulfate, concentrated and purified by silica gel column chromatography to obtain 1.90 g of 3-(2,6-dichlorophenyl)-4-phthalimide-1,2,5-thiadiazole.

m.p.: 214°–215° C.

$^1$H-NMR (CDCl$_3$, δppm) 7.15–7.4 (m, 3H), 7.55–7.95 (m, 4H).

IR (KBr, cm$^{-1}$) 1790, 1745, 1730, 1470, 1465, 1430, 1415, 1310, 710.

MS (m/z): 375 (M$^+$).

EXAMPLE 30

Preparation of 3-(2,6-dichlorophenyl)-4(3,3-dimethylureido)-1,2,5-thiadiazole (Compound No. 187)

To a solution of 0.49 g of 3-amino-4-(2,6-dichlorophenyl)-1,2,5-thiadiazole and 0.22 g of triethylamine in N,N-dimethylformamide, 0.24 g of dimethylcarbamoyl chloride was added and the mixture was heated at 120° C. for 12 hours. After allowing to cool, the mixture was poured into water and was extracted with ether. The ether layer was washed twice with dilute hydrochloric acid, twice with water and twice with saturated aqueous sodium chloride solution. The resultant was dried over anhydrous sodium sulfate, concentrated and purified by silica gel column chromatography to obtain 0.19 g of 3-(2,6-dichlorophenyl)-4(3,3-dimethylureido)-1,2,5-thiadiazole.

m.p.: 100°–103° C.

$^1$H-NMR (CDCl$_3$, δppm) 2.83 (s, 3H), 3.00 (s, 3H), 7.15–7.45 (m, 3H), 8.27 (s, 1H).

IR (KBr, cm$^{-1}$) 1630, 1460, 1425, 1380, 1115, 1100, 790, 775.

MS (m/z): 316 (M$^+$).

EXAMPLE 31

Preparation of 3-isobutyrylamino-4-(2,6-dichlorophenyl)-1,2,5-thiadiazole (Compound No. 188)

To a solution of 0.49 g of 3-amino-4-(2,6-dichlorophenyl)-1,2,5-thiadiazole and 0.22 g of triethylamine in N,N-dimethylformamide, 0.27 g of isobutyryl chloride was added and the mixture was heated at 60° C. for 12 hours. After allowing to cool, the mixture was poured into water and was extracted with ether. The ether layer was washed twice with dilute hydrochloric acid, twice with water and twice with saturated aqueous sodium chloride solution. The resultant was dried over anhydrous sodium sulfate, concentrated and purified by silica gel column chromatography to obtain 0.23 g of 3-isobutyrylamino-4-(2,6-dichlorophenyl)-1,2,5-thiadiazole m.p.: 112°–117° C.

$^1$H-NMR (CDCl$_3$, δppm) 1.08 (d, J=7Hz, 6H), 2.68 (septet, J=7Hz, 1H) 7.2–7.45 (m, 3H), 8.10 (bs, 1H).

IR (KBr, cm$^{-1}$) 3290, 1700, 1540, 1495, 1430, 1145.

MS (m/z): 315 (M$^+$).

EXAMPLE 32

Test for Evaluation of Effectiveness in Growth Inhibition of Weeds by Treatment of Water in Paddy Field The compounds with Compound Nos. 183–188 formulated into wettable powder according to Example 9 were tested for their effectiveness in growth inhibition of weeds in the same manner as in Example 12. The results are shown in Table 6.

TABLE 1

| Compound No. | X | V | Z | Y | A | Properties | NMR (60MHz) (δ ppm, CDCl$_3$) | IR (cm$^{-1}$, KBr) | Elementary Analysis: Found (Calcd.) % C | H | N |
|---|---|---|---|---|---|---|---|---|---|---|---|
| 1 | H | 3-Cl | 4-Cl | O | H | m.p. 235–240° C. | 7.50(d, J=8Hz, 1H), 8.07(dd, J=8Hz, 2Hz, 1H), 8.27(d, J=2Hz, 1H) (DMSO-d$_6$) | 3200–2400, 1525, 1225, 890, 855, 830 | (39.24) (38.88) | 1.82 (1.63) | 11.38 (11.33) |
| 2 | H | 3-Cl | 4-Cl | O | —C(=O)N(CH$_3$)$_2$ | m.p. 129–130° C. | 3.00(s, 3H), 3.17(s, 3H), 7.46(d, J=8Hz, 1H), 7.70(dd, J=8Hz, 2Hz, 1H), 7.97(d, J=2Hz, 1H) | 1745, 1370, 1140 | 41.80 (41.52) | 2.99 (2.85) | 13.15 (13.20) |
| 3 | H | 2-Cl | 4-Cl | O | H | m.p. 166–168° C. | 7.2–7.7(m) (DMSO-d$_6$) | 3200–2400, 1585, 1530, 1230, 885, 865, 825, 805 | 39.17 (38.88) | 1.54 (1.63) | 11.08 (11.33) |
| 4 | H | 2-Cl | 4-Cl | O | —C(=O)N(CH$_3$)$_2$ | Viscose Oil | 2.88(s, 3H), 2.98(s, 3H), 7.1–7.5(m, 3H) | 1745, 1370, 1150 (NaCl) | 41.89 (41.52) | 2.99 (2.85) | 12.80 (13.20) |
| 5 | H | 3-Cl | 4-Cl | O | —C(=O)N(pyrrolidine) | m.p. 134–135° C. | 1.8–2.3(m, 4H), 3.3–3.9(m, 4H), 7.43(d, J=8Hz, 1H), 7.70(dd, J=8Hz, 2Hz, 1H), 7.93(d, J=2Hz, 1H) | 1740, 1395, 1370, 1225, 1065, 835, 740 | 45.30 (45.36) | 3.41 (3.22) | 12.16 (12.20) |
| 6 | H | 2-Cl | 4-Cl | O | —C(=O)N(pyrrolidine) | Viscose Oil | 1.7–2.2(m, 4H), 3.2–3.8(m, 4H), 7.2–7.6(m, 3H) | 1750, 1370, 1225, 1080, 1050 (NaCl) | 45.31 (45.36) | 3.41 (3.22) | 12.15 (12.20) |
| 8 | H | 2-Cl | 6-Cl | O | —C(=O)N(pyrrolidine) | m.p. 74–75° C. | 1.6–2.1(m, 4H), 3.2–3.6(m, 4H), 7.2–7.45(m, 3H) | 1730, 1430, 1365, 1340, 1230, 1160, 785 | 45.58 (45.36) | 3.30 (3.22) | 12.38 (12.20) |
| 9 | H | 2-Cl | 6-Cl | O | —C(=O)N(C$_2$H$_5$)$_2$ | m.p. 105–106° C. | 1.03(t, J=7Hz, 6H), 3.26(broad q, J=7Hz, 4H), 7.2–7.45(m, 3H) | 1740, 1385, 1265, 1230, 1210, 1145, 860, 780 | 44.96 (45.09) | 3.95 (3.78) | 11.93 (12.13) |
| 10 | H | 2-Cl | 6-Cl | O | —C(=O)N(CH$_3$)(C$_4$H$_9^n$) | $n_D^{26.0}$ 1.5633 | 0.8–1.7(m, 7H), 2.88(s, 3H), 3.0–3.4(m, 2H), 7.2–7.45(m, 3H) | 1740, 1430, 1385, 1230, 1210, 1145, 790 (NaCl) | 47.02 (46.67) | 3.99 (4.19) | 11.52 (11.66) |
| 12 | H | 2-Cl | 6-Cl | O | —C(=O)N(C$_3$H$_7^i$)$_2$ | m.p. 103–104° C. | 1.18(d, J=7Hz, 12H), 13.4–4.3(m, 2H), 7.15–7.4(m, 3H) | 1740, 1430, 1300, 1230, 1040, 1020, 960, 795 | 48.45 (48.13) | 4.71 (4.57) | 11.39 (11.22) |
| 13 | H | 2-Cl | 6-Cl | O | —C(=O)N(piperidine) | m.p. 119–120° C. | 1.2–1.8(m, 6H), 3.1–3.6(m, 4H), 7.2–7.45(m, 3H) | 1735, 1430, 1380, 1215, 1140, 1020, 780 | 46.94 (46.93) | 3.49 (3.65) | 11.55 (11.72) |
| 14 | H | 2-Cl | 6-Cl | O | —C(=O)N(CH$_3$)(cyclohexyl) | m.p. 101–102° C. | 0.9–1.9(m, 10H), 2.75(s, 3H), 3.5–4.1(m, 1H), 7.15–7.4(m, 3H) | 2930, 1715, 1425, 1390, 1355, 1315, 1220, 1140, 1000, 800 | 49.86 (49.74) | 4.52 (4.43) | 11.18 (10.87) |

TABLE 1-continued

| Compound No. | X | V | Z | Y | A | Properties | NMR (60MHz) (δ ppm, CDCl₃) | IR (cm⁻¹, KBr) | Elementary Analysis: Found (Calcd.) % C | H | N |
|---|---|---|---|---|---|---|---|---|---|---|---|
| 15 | H | 2-Cl | 6-Cl | O | (piperidyl)—C(=O)— with methyl | m.p. 98–99° C. | 1.03(d, J=7Hz, 3H), 1.2–1.8(m, 6H), 2.6–3.2(m, 1H), 3.7–4.6(m, 2H), 7.2–7.45(m, 3H) | 1730, 1435, 1420, 1390, 1335, 1230, 1180, 1140, 1040, 785 | 48.70 (48.39) | 4.01 (4.06) | 11.15 (11.28) |
| 16 | H | 2-Cl | 6-Cl | O | (2,6-dimethylpiperidyl)—C(=O)— | m.p. 113–116° C. | 1.06(d, J=7Hz, 6H), 1.3–1.7(m, 6H), 3.9–4.5(m, 2H), 7.15–7.4(m, 3H) | 1725, 1390, 1335, 1300, 1225, 1060, 1030, 785 | 49.87 (49.74) | 4.27 (4.43) | 10.72 (10.87) |
| 17 | H | 2-Cl | 6-Cl | O | —C(=S)N(CH₃)₂ | m.p. 134–136° C. | 3.27(s, 6H), 7.2–7.45(m, 3H) | 1550, 1425, 1385, 1275, 1220, 1100, 790, 780 | 39.73 (39.52) | 2.86 (2.71) | 12.87 (12.57) |
| 18 | H | 2-Cl | 6-Cl | O | —C(=O)N(CH₃)(3-methoxyphenyl) | m.p. 91–93° C. | 3.23(s, 3H), 3.70(s, 3H), 6.4–7.4(m, 7H) | 1745, 1600, 1590, 1430, 1355, 1230, 1120, 790 | 50.08 (49.76) | 3.98 (3.19) | 10.61 (10.24) |
| 19 | H | 2-Cl | 6-Cl | O | —SO₂—C₆H₄—CH₃ | m.p. 107–108° C. | 2.37(s, 3H), 7.0–7.4(m, 5H), 7.70(d, J=8Hz, 2H) | 1390, 1195, 1180, 830, 740, 580, 545 | 44.99 (44.89) | 2.54 (2.51) | 6.88 (6.98) |
| 20 | H | 2-Cl | 6-Cl | O | —CH₂C(=O)—C₆H₅ | m.p. 101–103° C. | 5.57(s, 2H), 7.1–7.9(m, 8H) | 1700, 1480, 1430, 1395, 1225, 790 | 52.49 (52.61) | 2.86 (2.75) | 7.92 (7.67) |
| 21 | H | 2-Cl | 6-Cl | O | —CH₃ | m.p. 53–55° C. | 4.03(s, 3H), 7.1–7.35(m, 3H) | 1525, 1495, 1430, 1395, 1245, 1030, 790, 780 | 41.32 (41.39) | 2.11 (2.31) | 10.97 (10.72) |
| 22 | H | 2-Cl | 6-Cl | O | —CH₂—C₆H₅ | m.p. 70–71° C. | 5.40(s, 2H), 7.0–7.4(m, 8H) | 1520, 1480, 1430, 1365, 1310, 1245, 965, 790, 780, 750, 700 | 53.41 (53.42) | 2.99 (2.98) | 8.17 (8.30) |
| 23 | H | 2-Cl | 6-Cl | O | —C(=O)N(CH₃)(OCH₃) | m.p. 52–55° C. | 3.13(s, 3H), 3.57(s, 3H), 7.1–7.35(m, 3H) | 1750, 1430, 1360, 1230, 1115, 790 | 39.24 (39.53) | 2.54 (2.71) | 12.31 (12.57) |
| 24 | H | 2-Cl | 6-Cl | O | —C(=O)—morpholinyl | m.p. 92–94° C. | 3.2–3.8(m, 8H), 7.15–7.4(m, 3H) | 1755, 1730, 1430, 1390, 1210, 1120, 1050 | 43.57 (43.34) | 2.95 (3.07) | 11.28 (11.66) |
| 25 | H | 2-Cl | 6-Cl | O | —CH₂CH=CH₂ | n_D^26.2 1.5921 | 4.8–5.6(m, 4H), 5.7–6.3(m, 1H), 7.1–7.4(m, 3H) | 1560, 1515, 1480, 1430, 1405, 1240, 790 (NaCl) | 46.21 (46.00) | 2.92 (2.80) | 9.69 (9.75) |
| 26 | H | 2-Cl | 6-Cl | O | —CH₂C≡CH | m.p. 90–91° C. | 2.47(t, J=2Hz, 1H), 4.98(d, J=2Hz, 2H), 7.1–7.35(m, 3H) | 3300, 2130, 1480, 1365, 1245, 780 | 46.52 (46.33) | 2.22 (2.12) | 10.09 (9.82) |

TABLE 1-continued

| Compound No. | X | V | Z | Y | A | Properties | NMR (60MHz) (δ ppm, CDCl₃) | IR (cm⁻¹, KBr) | Elementary Analysis: Found (Calcd.) % C | H | N |
|---|---|---|---|---|---|---|---|---|---|---|---|
| 27 | H | 2-Cl | 6-Cl | O | —CHCOOH<br>\|<br>CH₃ | m.p. 176~177° C. | 1.52(d, J=7Hz, 3H), 5.25(q, J=Hz, 1H), 6.63(broad s, 1H), 7.40(s, 3H) (acetone-d₆) | 3200–2500, 1730, 1480, 1430, 1235, 790, 780 | 41.20 (41.39) | 2.59 (2.52) | 8.81 (8.77) |
| 28 | H | 2-Cl | 6-Cl | O | —CH₂COOH | m.p. 156~157° C. | 5.02(s, 2H), 7,43(s, 3H), 9.90(broad s, 1H) (acetone-d₆) | 3200–2400, 1735, 1485, 1430, 1395, 1260, 1240, 795 | 39.20 (39.36) | 1.84 (1.98) | 8.99 (9.18) |
| 29 | H | 2-F | 6-F | O | H | m.p. 165~166° C. | 6.7~7.6(m, 3H), 9.33(broad s, 1H) (acetone-d₆) | 3300–2500, 1470, 1005, 885 | 44.96 (44.86) | 1.73 (1.88) | 13.09 (13.07) |
| 30 | H | 2-F | 5-F | O | H | m.p. 180~181° C. | 7.1~7.7(m, 3H), 8.33(broad s, 1H) (acetone-d₆) | 3300–2500, 1480, 1470, 1250, 1185, 880, 875, 815 | 45.22 (44.86) | 1.84 (1.88) | 12.89 (13.07) |
| 31 | H | 2-F | 4-F | O | H | m.p. 181~184° C. | 6.8~7.3(m, 2H), 7.5~8.5(m, 2H) (acetone-d₆) | 3300–2500, 1535, 1470, 1260, 1150, 880, 860, 810 | 45.12 (44.86) | 1.74 (1.88) | 12.93 (13.07) |
| 32 | H | 3-F | 4-F | O | H | m.p. 205~208° C. | 7.1~7.6(m, 1H), 7.7~8.3(m, 2H) (acetone-d₆) | 3300–2400, 1525, 1425, 1285, 1260, 875 | 44.60 (44.86) | 2.07 (1.88) | 13.35 (13.07) |
| 33 | H | 2-F | 6-F | O | —CN(=O)(CH₃)(CH₃) | m.p. 77~78° C. | 2.90(s, 3H), 2.98(s, 3H), 6.7~7.6(m, 3H) | 1740, 1630, 1465, 1375, 1230, 1150, 1005 | 46.16 (46.31) | 3.27 (3.17) | 14.67 (14.73) |
| 34 | H | 2-F | 5-F | O | —CN(=O)(CH₃)(CH₃) | m.p. 86~87° C. | 2.93(s, 3H), 3.07(s, 3H), 6.9~7.5(m, 3H) | 1725, 1465, 1370, 1260, 1175, 1150, 870, 825, 765 | 46.26 (46.31) | 3.30 (3.17) | 15.10 (14.73) |
| 36 | H | 2-F | 4-F | O | —CN(=O)(CH₂)(CH₃) | n_D^{26.2} 1.5542 | 2.93(s, 3H), 3.05(s, 3H), 6.7~7.2(m, 2H), 7.4~7.85(m, 1H) | 1745, 1425, 1375, 1270, 1250, 1145, (NaCl) | 45.99 (46.31) | 3.32 (3.17) | 14.96 (14.73) |
| 37 | H | 3-F | 4-F | O | —CN(=O)(CH₃)(CH₃) | m.p. 76~77° C. | 3.03(s, 3H), 3.17(s, 3H), 6.9~7.9(m, 3H) | 1745, 1530, 1370, 1150, 1120 | 46.10 (46.31) | 3.15 (3.17) | 14.80 (14.73) |
| 39 | H | 2-Cl | 6-Cl | O | —C(=O)—C₃H₇ⁱ | m.p. 59~60° C. | 1.27(d, J=6Hz, 6H), 4.90(septet, J=6Hz, 1H), 7.2~7.5(m, 3H) | 1780, 1430, 1250, 1220, 1100, 910 | 45.56 (45.44) | 3.17 (3.17) | 8.76 (8.83) |
| 40 | H | 2-Cl | 6-Cl | O | —CO—C₃H₇ⁱ | n_D^{23.8} 1.5669 | 1.08(d, J=7Hz, 6H), 2.68(septet, J=7Hz, 1H), 7.2~7.5(m, 3H) | 1780, 1460, 1430, 1395, 1170, 1115, 790 (NaCl) | 43.27 (43.25) | 2.95 (3.02) | 8.17 (8.40) |

TABLE 1-continued

| Compound No. | X | V | Z | Y | A | Properties | NMR (60MHz) (δ ppm, CDCl₃) | IR (cm⁻¹, KBr) | Elementary Analysis: Found (Calcd.) % C | H | N |
|---|---|---|---|---|---|---|---|---|---|---|---|
| 41 | H | 2-Cl | 6-Cl | O | —CH₂OCH₃ | $n_D^{23.9}$ 1.5868 | 3.48(s, 3H), 5.50(s, 2H), 7.2~7.45(m, 3H) | 1520, 1485, 1430, 1380, 1165, 930 (NaCl) | 41.19 (41.25) | 2.60 (2.76) | 9.44 (9.62) |
| 42 | H | 3-F | 5-F | O | H | m.p. 234~136° C. | 6.8~7.3(m, 1H), 7.5~8.0(m, 2H) (DMSO-d₆) | 3300–2300, 1600, 1450, 1320, 1120, 990, 880 | 45.10 (44.86) | 1.85 (1.88) | 13.31 (13.07) |
| 43 | H | 2-Cl | 6-Cl | O | —Si(CH₃)₃ | $n_D^{23.8}$ 1.5488 | 0.33(s, 9H), 7.2~7.45(m, 3H) | 1485, 1430, 1255, 860, 790 (NaCl) | 40.99 (41.38) | 3.87 (3.78) | 8.64 (8.77) |
| 44 | H | 3-F | 5-F | O | —CN(CH₃)₂ ‖ O | m.p. 65~66° C. | 3.02(s, 3H), 3.17(s, 3H), 6.83(tt, J=8Hz, 2Hz, 1H), 7.2~7.7 (m, 2H) | 1725, 1600, 1380, 1305, 1150, 1130, 990 | 46.40 (46.31) | 3.05 (3.17) | 14.80 (14.73) |
| 45 | H | 2-Cl | 6-Cl | O | —COCH₃ ‖ O | m.p. 75~77° C. | 3.85(s, 3H), 7.2~7.5(m, 3H) | 1785, 1775, 1430, 1250, 1225, 780 | 39.10 (39.36) | 1.85 (1.98) | 9.41 (9.18) |
| 46 | H | 2-Cl | 6-Cl | O | —COC₂H₅ ‖ O | $n_D^{26.2}$ 1.5690 | 1.27(t, J=7Hz, 3H), 4.27(q, J=7Hz, 2H), 7.2~7.5(m, 3H) | 1785, 1430, 1245, 1215, 1010, 790 (NaCl) | 41.77 (41.39) | 2.57 (2.52) | 8.77 (8.77) |
| 47 | H | 2-Cl | 6-Cl | O | —CO—C(CH₃)₃ ‖ O | m.p. 95~96° C. | 1.43(s, 9H), 7.2~7.45(m, 3H) | 1775, 1270, 1255, 1230, 1145, 1115, 900, 790 | 44.75 (44.97) | 3.40 (3.48) | 7.78 (8.06) |
| 48 | H | 2-Cl | 6-Cl | O | —COCH₂—C₆H₅ ‖ O | Viscose Oil | 5.2(s, 2H), 7.2~7.5(m, 8H) | 1785, 1265, 1215 (NaCl) | 50.79 (50.40) | 2.82 (2.64) | 6.98 (7.34) |
| 49 | H | 2-Cl | 6-Cl | O | —CO—C₆H₅ ‖ O | Viscose Oil | 6.9~7.6(m) | 1800, 1240, 1215, 1190 (NaCl) | 48.80 (49.06) | 2.02 (2.19) | 7.52 (7.62) |
| 50 | H | 2-Cl | 6-Cl | O | —COCH₂CH₂OCH₃ ‖ O | m.p. 46~48° C. | 3.33(s, 3H), 3.45~3.7(m, 2H), 4.25~4.55(m, 2H), 7.2~7.5(m, 3H) | 1785, 1225, 1200 | 40.95 (41.27) | 2.73 (2.88) | 8.81 (8.02) |
| 51 | H | 2-Cl | 6-Cl | O | —COCH₂CCl₃ ‖ O | m.p. 114~115° C. | 4.80(s, 2H), 7.2~7.5(m, 3H) | 1795, 1435, 1400, 1215, 790, 760, 725 | 31.64 (31.27) | 1.36 (1.19) | 6.60 (6.63) |
| 52 | H | 2-Cl | 6-Cl | O | —C₃H₇ⁱ | $n_D^{26.0}$ 1.5747 | 1.33(d, J=6Hz, 6H), 5.17(septet, J=6Hz, 1H), 7.15~7.45(m, 3H) | 1480, 1430, 1250, 1110, 795 (NaCl) | 45.54 (45.68) | 3.34 (3.48) | 9.64 (9.68) |
| 53 | H | 2-Cl | 6-Cl | O | —C(CH₃)₃ | $n_D^{26.0}$ 1.5658 | 1.53(s, 9H), 7.2~7.45(m, 3H) | 1485, 1470, 1435, 1410, 1370, 1245, 1175, 795 (NaCl) | 47.61 (47.53) | 4.12 (3.98) | 9.13 (9.23) |

TABLE 1-continued

| Compound No. | X | V | Z | Y | A | Properties | NMR (60MHz) (δ ppm, CDCl$_3$) | IR (cm$^{-1}$, KBr) | Elementary Analysis: Found (Calcd.) % C | H | N |
|---|---|---|---|---|---|---|---|---|---|---|---|
| 54 | H | 2-Cl | 6-Cl | O | —Si(CH$_3$)$_2$—C(CH$_3$)$_3$ | m.p. 68~69° C. | 0.30(s, 6H), 0.82(s, 9H), 7.2~7.45(m, 3H) | 1485, 1475, 1435, 1255, 860, 845, 795 | 46.23 (46.53) | 4.82 (5.02) | 7.96 (7.75) |
| 55 | H | 2-Cl | 6-Cl | O | —C(=O)—C(CH$_3$)$_3$ | m.p. 83~86° C. | 1.13(s, 9H), 7.2~7.4(m, 3H) | 1765, 1430, 1395, 1085, 790, 780 | 46.78 (47.14) | 3.59 (3.65) | 8.51 (8.45) |
| 56 | H | 2-Cl | 6-Cl | O | —CH$_2$OCH$_2$CH$_2$—OCH$_3$ | $n_D^{26.0}$ 1.5657 | 3.33(s, 3H), 3.4~3.65(m, 2H), 3.7~4.0(m, 2H), 5.60(s, 2H), 7.2~7.5(m, 3H) | 1490, 1435, 1380, 1120, 1110, 930 (NaCl) | 43.35 (42.99) | 3.65 (3.60) | 8.04 (8.35) |
| 57 | H | 2-Cl | 6-Cl | O | —CH$_2$SCH$_3$ | m.p. 81~82° C. | 2.22(s, 3H), 5.47(s, 2H), 7.2~7.5(m, 3H) | 1480, 1430, 1400, 950, 790, 775 | 38.80 (39.09) | 2.45 (2.62) | 9.42 (9.11) |
| 58 | H | 2-Cl | 6-Cl | O | —CH$_2$-(2-NO$_2$-C$_6$H$_4$) | m.p. 118~120° C. | 5.87(s, 2H), 7.1~7.7(s, 6H), 7.8~8.2(m, 1H) | 1535, 1485, 1430, 1355, 795 | 47.39 (47.13) | 2.19 (2.37) | 10.98 (10.99) |
| 59 | H | 2-Cl | 6-Cl | O | —CH$_2$-(pyridyl) | m.p. 50~51° C. | 5.60(s, 2H), 7.0~7.8(m, 6H), 8.4~8.6(m, 1H) | 1490, 1430, 1415, 1365, 1250, 785, 750 | 49.54 (49.71) | 2.65 (2.68) | 12.68 (12.42) |
| 60 | H | 2-Cl | 6-Cl | O | —SO$_2$CH$_3$ | m.p. 78~80° C. | 3.45(s, 3H), 7.2~7.5(m, 3H) | 1430, 1395, 1365, 1180, 825, 780 | 33.00 (33.24) | 1.73 (1.85) | 8.50 (8.61) |
| 61 | H | 2-Cl | 6-Cl | O | —SO$_2$CF$_3$ | $n_D^{26.0}$ 1.5303 | 7.25~7.5(m) | 1435, 1385, 1220, 1135, 1015, 840, 610 (NaCl) | 28.55 (28.51) | 0.77 (0.79) | 7.66 (7.38) |
| 63 | H | 2-Cl | 6-Cl | O | —C(=O)N(CH$_3$)(CH$_2$)$_3$OC$_2$H$_5$ | $n_D^{26.3}$ 1.5560 | 1.12(t, J=7Hz, 3H), 1.4~2.0(m, 2H), 2.92(broad s, 3H), 3.1~3.7(m, 6H), 7.2~7.5(m, 3H) | 1750, 1435, 1385, 1235, 1200, 1115, 790 (NaCl) | 46.55 (46.16) | 4.37 (4.39) | 10.36 (10.76) |
| 64 | H | 2-Cl | 6-Cl | O | —CO—CH$_2$CH=CH$_2$ | $n_D^{26.6}$ 1.5715 | 4.5~4.8(m, 2H), 5.0~6.2(m, 3H), 7.2~7.5(m, 3H) (NaCl) | 1785, 1430, 1215, | 43.41 (43.52) | 2.50 (2.43) | 8.44 (8.45) |
| 65 | H | 2-Cl | 6-Cl | O | —CO—C$_4$H$_9^i$ | m.p. 57~58° C. | 0.87(d, J=7Hz, 6H), 1.6~2.3(m, 1H), 4.00(d, J=7Hz, 2H), 7.2~7.5(m, 3H) | 1785, 1435, 1215 | 45.08 (44.97) | 3.63 (3.48) | 8.36 (8.06) |
| 67 | H | 2-Cl | 6-Cl | O | —C(=O)-cyclopropyl | m.p. 67~68° C. | 0.7~1.2(m, 4H), 1.3~1.9(m, 1H), 7.2~7.5(m, 3H) | 1765, 1375, 1125, 1085, 785 | 46.10 (45.73) | 2.44 (2.55) | 8.82 (8.88) |
| 68 | H | 2-Cl | 6-Cl | O | —CO—N=C(CH$_3$)$_2$ | Viscose Oil | 1.97(s, 3H), 2.00(s, 3H), 7.2~7.5(m, 3H) | 1820–1780, 1560, 1430, 1400, 1280, 1240–1160 (NaCl) | 41.44 (41.63) | 2.58 (2.62) | 11.99 (12.13) |

TABLE 1-continued

| Compound No. | X | V | Z | Y | A | Properties | NMR (60MHz) (δ ppm, CDCl₃) | IR (cm⁻¹, KBr) | Elementary Analysis: Found (Calcd.) % | | |
|---|---|---|---|---|---|---|---|---|---|---|---|
| | | | | | | | | | C | H | N |
| 69 | H | 2-Cl | 6-Cl | O | 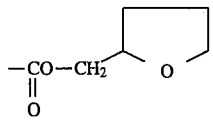 | Viscose Oil | 1.5~2.2(m, 4H), 3.6~4.4(m, 5H), 7.2~7.5(m, 3H) | 1785, 1435, 1220 (NaCl) | 44.76 (44.81) | 3.41 (3.22) | 7.54 (7.46) |
| 70 | H | 2-Cl | 6-Cl | O | 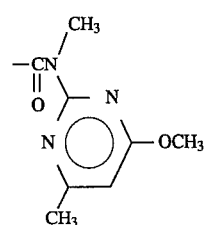 | Viscose Oil | 2.30(s, 3H), 3.43(s, 3H), 3.80(s, 3H), 6.30(s, 1H), 7.2~7.5(m, 3H) | 1755, 1600, 1560, 1435, 1365, 1100 (NaCl) | 45.32 (45.08) | 3.05 (3.07) | 16.68 (16.42) |
| 71 | H | 2-Cl | 6-Cl | O | 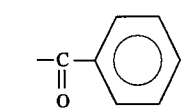 | m.p. 111~112° C. | 7.2~8.2(m) | 1750, 1225, 1060 | 50.92 (51.29) | 2.33 (2.29) | 8.29 (7.97) |
| 72 | H | 2-Cl | 6-Cl | O | 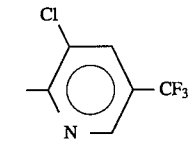 | m.p. 99~100° C. | 7.15~7.4(m, 3H), 7.8~8.0(m, 1H), 8.15~8.35(m, 1H) | 1390, 1330, 1295, 1155, 1140, 1070 | 39.57 (39.41) | 1.23 (1.18) | 9.98 (9.84) |
| 73 | H | 2-Me | 6-Me | O | H | m.p. 134~135° C. | 2.13(s, 6H), 6.8~7.4(m, 3H) | 3300-2400, 1530, 1460, 1225, 875, 765 | 58.42 (58.23) | 4.91 (4.88) | 13.82 (13.58) |
| 74 | 2-Cl | 3-Cl | 6-Cl | O | H | m.p. 157~160° C. | 7.37(d, J=9Hz, 1H), 7.50(d, J=9Hz, 1H), 9.75(broad s, 1H) (acetone-d₆) | 3300-2400, 1535, 1495, 1220, 1180, 815, 790 | 34.48 (34.12) | 1.02 (1.07) | 9.83 (9.94) |
| 76 | H | 2-Cl | 6-Cl | O | 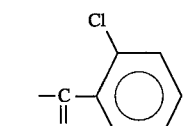 | m.p. 104~106° C. | 7.1~7.5(m, 6H), 7.7~8.0(m, 1H) | 1770, 1230, 1140 | 46.81 (46.71) | 1.83 (1.82) | 7.60 (7.26) |
| 77 | H | 2-Cl | 6-Cl | O | 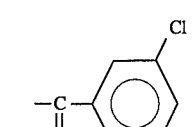 | m.p. 83~86° C. | 7.0~7.7(m, 5H), 7.7~8.0(m, 2H) | 1775, 1760, 1225 | 46.47 (46.71) | 1.66 (1.82) | 7.10 (7.26) |
| 78 | H | 2-Cl | 6-Cl | O | 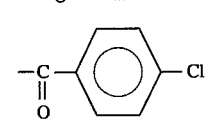 | m.p. 137~138° C. | 7.2~7.6(m, 5H), 7.93(d, J=8Hz, 2H) | 1770, 1230, 1150 | 46.51 (46.71) | 1.76 (1.82) | 7.58 (7.26) |
| 79 | H | 2-Cl | 6-Cl | O | 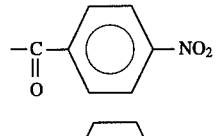 | m.p. 131~133° C. | 7.2~7.4(m, 3H), 8.1~8.3(m, 4H) | 1765, 1530, 1230, 1165 | 45.85 (45.47) | 1.82 (1.78) | 10.73 (10.60) |
| 80 | H | 2-Cl | 6-Cl | O | 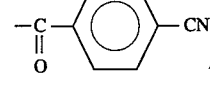 | m.p. 138~140° C. | 7.25~7.5(m, 3H), 7.75(d, J=8Hz, 2H), 8.10(d, J=8Hz, 2H) | 2240, 1760, 1260, 1230, 1060 | 51.41 (51.08) | 2.06 (1.87) | 11.08 (11.16) |

TABLE 1-continued

| Compound No. | X | V | Z | Y | A | Properties | NMR (60MHz) (δ ppm, CDCl₃) | IR (cm⁻¹, KBr) | Elementary Analysis: Found (Calcd.) % C | H | N |
|---|---|---|---|---|---|---|---|---|---|---|---|
| 81 | H | 2-Cl | 6-Cl | O | —C(=O)—C₆H₄—CH₃ (para) | m.p. 140~141° C. | 2.37(s, 3H), 7.0~7.3(m, 5H), 7.80(d, J=8Hz, 2H) | 1755, 1270, 1185, 1065 | 52.22 (52.61) | 2.79 (2.75) | 7.50 (7.67) |
| 82 | H | 2-Cl | 6-F | O | H | m.p. 142~144° C. | 7.1~7.8(m) (acetone-d₆) | 3300~2500, 1535, 1520, 1510, 1445, 1230, 880 | 41.73 (41.66) | 1.88 (1.74) | 12.46 (12.14) |
| 83 | H | 2-Cl | 6-F | O | —C(=O)N(CH₃)₂ | m.p. 67~68° C. | 2.88(s, 3H), 2.97(s, 3H), 6.8~7.5(m, 3H) | 1750, 1375, 1150 (NaCl) | 43.63 (43.78) | 3.04 (3.00) | 13.65 (13.92) |
| 84 | H | 2-Cl | 6-F | O | —C(=O)—C₃H₇ⁱ | Viscose Oil | 1.13(d, J=7Hz, 6H), 2.70(septet, J=7Hz, 1H), 6.8~7.4(m, 3H) | 1780, 1455, 1405, 1080 (NaCl) | 47.72 (47.92) | 3.54 (3.35) | 9.21 (9.31) |
| 85 | H | 2-Cl | 6-Cl | O | —C(=O)—C₆H₄—OCH₃ (para) | m.p. 105~106° C. | 3.83(s, 3H), 6.87(d, J=9Hz, 2H), 7.1~7.4(m, 3H), 7.92(d, J=9Hz, 2H) | 1745, 1260, 1170 | 50.38 (50.40) | 2.50 (2.64) | 7.34 (7.34) |
| 86 | H | 2-Cl | 6-Cl | O | —C(=O)—C₃H₇ⁿ | Viscose Oil | 0.80(t, J=7Hz, 3H), 1.2~1.9(m, 2H), 2.43(t, J=7Hz, 2H), 7.3~7.5(m, 3H) | 1790, 1440, 1400, 1235, 1085 (NaCl) | 45.33 (45.44) | 3.09 (3.17) | 9.09 (8.83) |
| 87 | H | 2-Cl | 6-Cl | O | —C(=O)—C₄H₉ⁿ | Viscose Oil | 0.6~1.9(m, 7H), 2.43(t, J=7Hz, 2H), 7.2~7.5(m, 3H) | 1790, 1435, 1400, 1080 (NaCl) | 47.18 (47.14) | 3.64 (3.65) | 8.47 (8.45) |
| 88 | H | 2-Cl | 6-Cl | O | —C(=O)—C₄H₉ⁱ | $n_D^{25.2}$ 1.5592 | 0.82(d, J=6Hz, 6H), 1.5~2.5(m, 3H), 7.2~7.5(m, 3H) | 1785, 1435, 1400, 1080 (NaCl) | 47.48 (47.14) | 3.77 (3.65) | 8.60 (8.45) |
| 89 | H | 2-Cl | 6-Cl | O | —C(=O)—C₆H₄—Br | m.p. 100~101° C. | 7.1~7.5(m, 4H), 7.5~8.3(m, 3H) | 1775, 1760, 1435, 1230, 1050 | 42.23 (41.88) | 1.57 (1.64) | 6.50 (6.51) |
| 90 | H | 2-Cl | 6-Cl | O | —C(=O)—C₆H₄—CH₃ | m.p. 87~88° C. | 2.37(s, 3H), 7.1~7.5(m, 5H), 7.6~7.9(m, 2H) | 1755, 1265, 1230, 1190, 1050 | 52.54 (52.61) | 2.94 (2.75) | 7.65 (7.67) |
| 91 | H | 2-Cl | 6-Cl | O | —C(=O)—C₆H₄—NO₂ | m.p. 102~103° C. | 7.2~7.4(m, 3H), 7.63(t, J=8Hz, 1H), 8.2~8.6(m, 2H), 8.78(t, J=2Hz, 1H) | 1760, 1535, 1225 | 45.07 (45.47) | 1.61 (1.78) | 10.27 (10.60) |

TABLE 1-continued

| Compound No. | X | V | Z | Y | A | Properties | NMR (60MHz) (δ ppm, CDCl$_3$) | IR (cm$^{-1}$, KBr) | Elementary Analysis: Found (Calcd.) % | | |
|---|---|---|---|---|---|---|---|---|---|---|---|
| | | | | | | | | | C | H | N |
| 92 | H | 2-Cl | 6-Cl | O | —C(=O)—C$_6$H$_4$—F | m.p. 91~93° C. | 7.1~7.9(m) | 1765, 1270, 1230, 1180, 1060 | 49.01 (48.79) | 2.03 (1.91) | 7.29 (7.58) |
| 93 | H | 2-Cl | 6-Cl | O | —C(=O)—C$_6$H$_3$—Cl,Cl | m.p. 121~122° C. | 7.2~7.5(m, 3H), 7.55(t, J=1.5Hz, 1H), 7.86(d, J=1.5 Hz, 2H) | 1760, 1435, 1250, 1225 | 42.63 (42.88) | 1.51 (1.43) | 6.91 (6.66) |
| 94 | H | 2-Cl | 6-Cl | O | —C(=O)—C$_6$H$_4$—CF$_3$ | m.p. 84~85° C. | 7.2~8.0(m, 5H), 8.1~8.4(m, 2H) | 1770, 1330, 1220, 1170, 1135, 1075, 1060 | 45.46 (45.84) | 1.77 (1.68) | 6.41 (6.68) |
| 95 | H | 2-Cl | 6-Cl | 0 | —C(=O)—C$_6$H$_4$—CN | m.p. 144~146° C. | 7.2~8.0(m, 5H), 8.1~8.4(m, 2H) | 2215, 1765, 1430, 1395, 1260, 1230, 1160, 1065 | 51.07 (51.08) | 1.94 (1.87) | 11.27 (11.16) |
| 96 | H | 2-Cl | 6-Cl | O | —C(=O)—C$_6$H$_4$—OCH$_3$ | m.p. 78~80° C. | 3.78(s, 3H), 7.0~7.7(m, 7H) | 1690, 1315, 1295 | 50.01 (50.40) | 2.74 (2.64) | 6.97 (7.34) |
| 97 | H | 2-Cl | 6-Cl | O | —CH$_2$C(=O)N(CH$_3$)—C$_6$H$_5$ | m.p. 133~136° C. | 3.27(s, 3H), 4.73 (s, 2H), 7.1~7.5 (m, 8H) | 1675, 1520, 1485, 1410 | 51.68 (51.78) | 3.12 (3.32) | 10.29 (10.65) |
| 98 | H | 2-Cl | 6-Cl | O | —CH$_2$C(=O)NH—C$_6$H$_5$ | m.p. 118~121° C. | 5.02(s, 2H), 7.0~7.6(m, 8H), 7.93(bs, 1H) | 1680, 1485, 1410 | 50.17 (50.54) | 2.85 (2.91) | 11.23 (11.05) |
| 99 | 2-MeO | 3-Cl | 6-MeO | O | H | m.p. 118~120° C. | 3.68(s, 3H), 3.73 (s, 3H), 6.77(d, J=9 Hz, 1H), 7.37(d, J=9 Hz, 1H) (acetone-d$_6$) | 3400~2600, 1540, 1470, 1295, 1230, 1100 | 44.29 (44.04) | 3.16 (3.32) | 9.88 (10.27) |
| 100 | H | 2-Cl | 5-Cl | O | H | m.p. 117~118° C. | 7.4~7.6(m) (acetone-d$_6$) | 3200~2400, 1540, 1455, 1110, 810 | 39.09 (38.88) | 1.62 (1.63) | 11.10 (11.33) |
| 101 | H | 2-Cl | 6-Me | O | H | m.p. 131~132° C. | 2.10(s), 7.33(s) (acetone-d$_6$) | 3300~2400, 1505, 1455 | 47.50 (47.68) | 3.15 (3.11) | 12.36 (12.35) |

TABLE 1-continued

| Compound No. | X | V | Z | Y | A | Properties | NMR (60MHz) (δ ppm, CDCl₃) | IR (cm⁻¹, KBr) | Elementary Analysis: Found (Calcd.) % C | H | N |
|---|---|---|---|---|---|---|---|---|---|---|---|
| 102 | H | 2-Cl | 5-Cl | O | −CN(=O)(CH₃)(CH₃) | m.p. 87~90° C. | 2.93(s, 6H), 7.2~7.5(m, 3H) | 1730, 1665, 1095 | 41.73 (41.52) | 2.71 (2.85) | 13.57 (13.20) |
| 103 | H | 2-Cl | 6-Me | O | −CN(=O)(CH₃)(CH₃) | m.p. 89~90° C. | 2.13(s, 3H), 2.80(s, 3H), 2.90(s, 3H), 7.0~7.3(m, 3H) | 1745, 1370, 1150 | 48.64 (48.40) | 4.13 (4.06) | 13.72 (14.11) |
| 105 | 2-Cl | 3-NO₂ | 6-Cl | O | H | m.p. 192~194° C. | 7.78(d, J=9Hz, 1H), 8.08(d, J=9Hz, 1H) (acetone-d₆) | 3200~2400, 1535, 1350, 870 | 33.13 (32.89) | 1.07 (1.03) | 14.37 (14.38) |
| 106 | 2-Cl | 3-NO₂ | 6-Cl | O | −C(=O)−C₃H₇ⁱ | Viscose Oil | 2.13(d, J=7Hz, 6H), 2.73(septet, J=7Hz, 1H), 7.57(d, J=9Hz, 1H), 7.88(d, J=9Hz, 1H) | 1780, 1540, 1370, 1350, 1070 (NaCl) | 39.78 (39.79) | 2.48 (2.50) | 11.34 (11.60) |
| 107 | 2-Cl | 3-NO₂ | 6-Cl | O | −CN(=O)(CH₃)(CH₃) | m.p. 93~95° C. | 2.90(s, 3H), 2.98(s, 3H), 7.53(d, J=8.5Hz, 1H), 7.83(d, J=8.5Hz, 1H) | 1735, 1540, 1360, 1150 | 36.18 (36.37) | 2.11 (2.22) | 15.37 (15.42) |
| 108 | H | 2-F | 6-F | O | −COCH₃ | m.p. 39~41° C. | 3.84(s, 3H), 6.75~7.65(m, 3H) | 1790, 1470, 1260, 1225, 1005 | 43.86 (44.12) | 2.24 (2.22) | 10.36 (10.29) |
| 109 | H | 3-F | 4-F | O | −COCH₃ | m.p. 49~50° C. | 3.97(s, 3H), 7.20(m, 1H), 7.73(m, 2H) | 1880, 1790, 1530, 1430, 1290, 1275, 1240, 1220 | 44.25 (44.12) | 2.03 (2.22) | 10.14 (10.29) |
| 110 | 2-F | 3-NO₂ | 6-F | O | −COCH₃ | m.p. 90~92° C. | 3.90(s, 3H), 7.18 (ddt, J=1.5Hz, 8Hz, 8Hz, 1H), 8.24(ddt, J=5.5Hz, 9Hz, 9Hz, 1H) | 1805, 1795, 1540, 1360, 1250, 1220, 1190 | 37.89 (37.86) | 1.41 (1.58) | 13.38 (13.24) |
| 111 | 2-F | 3-NO₂ | 6-F | O | H | m.p. 152~154° C. | 7.22(ddt, J=1.5Hz, 8Hz, 8Hz, 1H), 8.23 (ddt, J=5, 5Hz, 9Hz, 9Hz, 1H) (acetone-d₆) | 3300~2500, 1535, 1475, 1360 | 37.06 (37.07) | 1.16 (1.16) | 15.90 (16.21) |
| 112 | 2-NO₂ | 4-F | 5-F | O | −COCH₃ | $n_D^{26.1}$ 1.5560 | 3.87(s, 3H), 7.2~7.6(m, 1H), 7.98(dd, J=7Hz, 9Hz, 1H) | 1790, 1550, 1350, 1305, 1250, 1225, 1210, 1190 | 37.91 (37.86) | 1.58 (1.58) | 13.57 (13.24) |
| 113 | 2-NO₂ | 3-F | 4-F | O | H | m.p. 213~214° C. | 7.75(dd, J=7Hz, 10 Hz, 1H), 8.15(dd, J=7 Hz, 10Hz, 1H) (acetone-d₆) | 3200~2400, 1550, 1520, 1345, 1320 | 36.83 (37.07) | 1.01 (1.16) | 16.44 (16.21) |
| 114 | H | 2-NO₂ | 3-CF₃ | O | −COCH₃ | m.p. 82~83° C. | 3.87(s, 3H), 7.7~8.3(m, 3H) | 1790, 1535, 1220 | 37.61 (37.83) | 1.85 (1.73) | 12.26 (12.03) |
| 115 | H | 2-NO₂ | 5-CF₃ | O | −COCH₃ | m.p. 41~43° C. | 3.99(s3H), 7.8~8.1(m, 1H), 8.2~8.5(m, 2H) | 1790, 1545, 1260, 1220 | 38.07 (37.83) | 1.67 (1.73) | 12.30 (12.03) |
| 116 | H | 2-Cl | 6-Cl | O | −CO(=S)−C₆H₅ | m.p. 93~94° C. | 6.8~7.6(m) | 1490, 1435, 1390, 1290, 1175, 790 | 46.60 (47.00) | 2.09 (2.10) | 7.11 (7.30) |

TABLE 1-continued

| Compound No. | X | V | Z | Y | A | Properties | NMR (60MHz) (δ ppm, CDCl$_3$) | IR (cm$^{-1}$, KBr) | Elementary Analysis: Found (Calcd.) % | | |
|---|---|---|---|---|---|---|---|---|---|---|---|
| | | | | | | | | | C | H | N |
| 117 | H | 2-Br | 6-Cl | O | H | m.p. 200~205° C. | 7.2~7.8(m) (acetone-d$_6$) | 3300~2400, 1535, 1510, 1430, 880, 770 | 32.76 (32.94) | 1.26 (1.38) | 9.79 (9.60) |
| 118 | H | 2-NO$_2$ | 5-CF$_3$ | O | H | m.p. 211~212° C. | 8.10(d, J=9Hz, 1H), 8.4~9.0(m, 2H) (acetone-d$_6$) | 3300~2400, 1595, 1535, 1345, 1155, 1135 | 37.02 (37.12) | 1.37 (1.38) | 14.28 (14.42) |
| 119 | H | 2-Br | 6-Cl | O | —COCH$_3$ (=O) | m.p. 77~80° C. | 3.93(s, 3H), 7.0~7.8(m, 3H) | 1770, 1440, 1260, 1225 | 34.38 (34.35) | 1.56 (1.72) | 7.97 (8.01) |
| 120 | H | 2-NO$_2$ | 5-F | O | —COCH$_3$ (=O) | $n_D^{25.1}$ 1.5762 | 3.87(s, 3H), 7.0~7.4(m, 2H), 8.13(dd, J=5Hz, 10Hz, 1H) | 1790, 1590, 1530, 1440, 1350, 1280, 1230, 1190 (NaCl) | 39.97 (40.13) | 1.94 (2.02) | 14.40 (14.04) |
| 121 | H | 2-Cl | 5-Cl | O | —COCH$_3$ (=O) | $n_d^{25.2}$ 1.5883 | 3.87(s, 3H), 7.3~7.5(m, 3H) | 1785, 1435, 1245, 1220, 1100, 1020, 935 (NaCl) | 39.46 (39.36) | 2.01 (1.98) | 9.56 (9.18) |
| 122 | H | 2-NO$_2$ | 5-CF$_3$ | O | 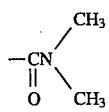 | m.p. 103~104° C. | 3.04(s, 3H), 3.17(s, 3H), 7.94(d, J=8Hz, 1H), 8.1~8.4(m, 2H) | 1750, 1545, 1370, 1140 | 40.01 (39.78) | 2.46 (2.50) | 15.14 (15.46) |
| 123 | H | 2-NO$_2$ | 5-Cl | O | H | m.p. 194~204° C. | 7.8~8.1(m, 2H), 8.2~8.5(m, 1H) (acetone-d$_6$) | 3300~2400, 1595, 1580, 1525, 1350, 850 | 39.75 (39.76) | 1.49 (1.66) | 17.19 (17.38) |
| 124 | H | 2-Cl | 6-Cl | O | 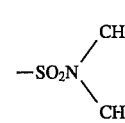 | $n_D^{27.3}$ 1.5748 | 2.97(s, 6H), 7.3~7.5(m, 3H) | 1430, 1390, 1180, 740 (NaCl) | 33.72 (33.90) | 2.67 (2.56) | 12.07 (11.86) |
| 125 | H | 2-Cl | 6-Cl | O | 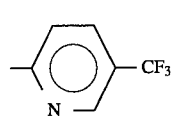 | $n_D^{27.2}$ 1.5741 | 7.16(d, J=8.5Hz, 1H), 7.27(s, 3H), 7.90(dd, J=2.5Hz, 8.5Hz, 1H), 8.42(bs, 1H) | 1610, 1390, 1325, 1245, 1130 (NaCl) | 42.95 (42.87) | 1.56 (1.54) | 10.94 (10.71) |
| 126 | H | 2-Cl | 6-Cl | O | 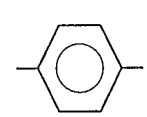 | m.p. 149~154° C. | 7.0~7.5(m) | 1485, 1465, 1400, 1245 | 47.22 (47.01) | 1.92 (1.97) | 7.75 (7.83) |
| 127 | H | 2-Cl | 6-Cl | O | 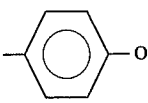 | m.p. 89~91° C. | 3.77(s, 3H), 6.7~7.5(m, 7H) | 1505, 1465, 1400, 1240, 1195 | 51.36 (51.00) | 2.66 (2.85) | 7.97 (7.93) |
| 128 | 3-Br | 4-OH | 5-Br | O | CH$_3$ | m.p. 207~210° C. | 4.22(s, 3H), 8.23(s, 2H) (acetone-d$_6$) | 3350, 1405, 1395, 1245, 1130 | 29.31 (29.53) | 1.53 (1.65) | 7.67 (7.65) |
| 129 | H | 2-NO$_2$ | 5-F | O | 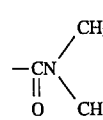 | m.p. 125~126° C. | 2.89(s, 3H), 2.97(s, 3H), 7.1~7.5(m, 2H), 8.13(dd, J=4Hz, 9Hz, 1H) | 1750, 1520, 1370, 1350, 1150 | 42.32 (42.30) | 2.89 (2.90) | 17.95 (17.94) |

TABLE 1-continued

| Compound No. | X | V | Z | Y | A | Properties | NMR (60MHz) (δ ppm, CDCl$_3$) | IR (cm$^{-1}$, KBr) | Elementary Analysis: Found (Calcd.) % | | |
|---|---|---|---|---|---|---|---|---|---|---|---|
| | | | | | | | | | C | H | N |
| 130 | H | 2-NO$_2$ | 5-Cl | O | —COCH$_3$ ‖ O | $n_D^{25.2}$ 1.5997 | 3.88(s, 3H), 7.4~7.7(m, 2H), 8.07(d, J=9Hz, 1H) | 1790, 1570, 1535, 1435, 1345, 1250, 1220 | 38.16 (38.04) | 2.01 (1.91) | 13.38 (13.31) |

TABLE 2

| Compound No. | Amount of Compound g/10a | Damage to Crop Rice | Barnyardgrass | Small Flower Umbrellaplant | Bulrush | Monochoria | Broadleaved |
|---|---|---|---|---|---|---|---|
| 1 | 125 | 0 | 0 | 0 | 0 | 0 | 0 |
| | 250 | 0 | 0 | 0 | 0 | 0 | 0 |
| 2 | 125 | 0 | 2 | 4 | 2 | 5 | 4 |
| | 250 | 0 | 3 | 5 | 3 | 5 | 4 |
| 3 | 125 | 0 | 0 | 3 | 0 | 0 | 0 |
| | 250 | 0 | 1 | 5 | 0 | 0 | 3 |
| 4 | 125 | 0 | 1 | 5 | 1 | 5 | 4 |
| | 250 | 0 | 4 | 5 | 4 | 5 | 5 |
| 5 | 125 | 0 | 3 | 5 | 0 | 4 | 2 |
| | 250 | 0 | 4 | 5 | 0 | 5 | 2 |
| 6 | 125 | 0 | 2 | 4 | 2 | — | 2 |
| | 250 | 0 | 3 | 5 | 3 | — | 5 |
| 7 | 125 | 0 | 4.5 | 5 | 5 | — | 5 |
| | 250 | 0 | 5 | 5 | 5 | — | 5 |
| 8 | 125 | 0 | 5 | 5 | 3 | — | 5 |
| | 250 | 0 | 5 | 5 | 4 | — | 5 |
| 9 | 125 | 0 | 3 | 5 | 2 | — | 5 |
| | 250 | 0 | 4 | 5 | 2 | — | 5 |
| 10 | 125 | 0 | 4 | 5 | 2 | — | 5 |
| | 250 | 0 | 5 | 5 | 2 | — | 5 |
| 11 | 125 | 0 | 4 | 5 | 5 | — | 5 |
| | 250 | 0 | 5 | 5 | 5 | — | 5 |
| 12 | 125 | 0 | 3 | 5 | 2 | — | 3 |
| | 250 | 0 | 3 | 5 | 2 | — | 5 |
| 13 | 125 | 0 | 5 | 5 | 4.5 | — | 5 |
| | 250 | 0 | 5 | 5 | 5 | — | 5 |
| 14 | 125 | 0 | 3 | 5 | 2 | — | 5 |
| | 250 | 0 | 4 | 5 | 3 | — | 5 |
| 15 | 125 | 0 | 4 | 5 | 1 | — | 4 |
| | 250 | 0 | 4 | 5 | 2 | — | 5 |
| 16 | 125 | 0 | 4 | 5 | 2 | — | 2 |
| | 250 | 0 | 4 | 5 | 2 | — | 2 |
| 17 | 125 | 0 | 3 | 5 | 3 | — | 5 |
| | 250 | 0 | 4.5 | 5 | 3 | — | 5 |
| 18 | 125 | 0 | 3 | 5 | 2 | — | 5 |
| | 250 | 0 | 4.5 | 5 | 2 | — | 5 |
| 19 | 125 | 0 | 3 | 5 | 3 | — | 5 |
| | 250 | 0 | 4.5 | 5 | 3 | — | 5 |
| 20 | 125 | 0 | 3 | 3 | 2 | — | 0 |
| | 250 | 0 | 3 | 5 | 2 | — | 0 |
| 21 | 125 | 0 | 2 | 4 | 1 | — | 0 |
| | 250 | 0 | 2 | 4 | 1 | — | 3 |
| 22 | 125 | 0 | 2 | 5 | 3 | — | 2 |
| | 250 | 0 | 2 | 5 | 3 | — | 3 |
| 23 | 125 | 0 | 3 | 5 | 5 | — | 5 |
| | 250 | 0 | 4.5 | 5 | 5 | — | 5 |
| 24 | 125 | 0 | 4.5 | 5 | 4 | — | 5 |
| | 250 | 0 | 5 | 5 | 5 | — | 5 |
| 25 | 125 | 0 | 3 | 5 | 2 | — | 0 |
| | 250 | 0 | 3 | 5 | 2 | — | 0 |
| 26 | 125 | 0 | 4.5 | 5 | 1 | — | 2 |
| | 250 | 0 | 5 | 5 | 3 | — | 3 |
| 27 | 125 | 0 | 3 | 5 | 0 | — | 2 |
| | 250 | 0 | 3 | 5 | 0 | — | 2 |
| 28 | 125 | 0 | 3 | 5 | 2 | — | 5 |
| | 250 | 0 | 3 | 5 | 2 | — | 5 |
| 29 | 125 | 0 | 0 | 5 | 0 | 0 | 0 |
| | 250 | 0 | 0 | 5 | 1 | 0 | 0 |

TABLE 2-continued

| Compound No. | Amount of Compound g/10a | Damage to Crop Rice | Barn-yard-grass | Small Flower Umbrella-plant | Bul-rush | Mono-choria | Broad-leaved |
|---|---|---|---|---|---|---|---|
| 30 | 125 | 0 | 0 | 0 | 2 | 0 | 0 |
|    | 250 | 0 | 0 | 1 | 2 | 0 | 0 |
| 31 | 125 | 0 | 0 | 3 | 0 | 0 | 0 |
|    | 250 | 0 | 0 | 5 | 1 | 0 | 0 |
| 32 | 125 | 0 | 0 | 0 | 2 | 0 | 0 |
|    | 250 | 0 | 0 | 0 | 2 | 0 | 0 |
| 33 | 125 | 0 | 0 | 5 | 0 | 3 | 2 |
|    | 250 | 0 | 2 | 5 | 2 | 3 | 5 |
| 34 | 125 | 0 | 3 | 5 | 1 | 1 | 2 |
|    | 250 | 0 | 3 | 5 | 2 | 1 | 2 |
| 35 | 125 | 0 | 3 | 5 | 2 | 2 | 5 |
|    | 250 | 0 | 3 | 5 | 2 | 2 | 5 |
| 36 | 125 | 0 | 2 | 5 | 0 | 0 | 2 |
|    | 250 | 0 | 2 | 5 | 2 | 2 | 3 |
| 37 | 125 | 0 | 2 | 5 | 3 | 2 | 5 |
|    | 250 | 0 | 4 | 5 | 4 | 5 | 5 |
| 38 | 125 | 0 | 0 | 2 | 0 | 0 | 2 |
|    | 250 | 0 | 0 | 2 | 0 | 0 | 2 |
| 39 | 125 | 0 | 4 | 5 | 5 | 2 | 5 |
|    | 250 | 0 | 4 | 5 | 5 | 2 | 5 |
| 40 | 125 | 0 | 3 | 5 | 5 | 5 | 5 |
|    | 250 | 0 | 4.5 | 5 | 5 | 5 | 5 |
| 41 | 125 | 0 | 3 | 5 | 5 | 0 | 5 |
|    | 250 | 0 | 4 | 5 | 5 | 5 | 5 |
| 42 | 125 | 0 | 1 | 4 | 0 | 2 | 0 |
|    | 250 | 0 | 2 | 5 | 0 | 2 | 1 |
| 43 | 125 | 0 | 0 | 4 | 4 | 0 | 5 |
|    | 250 | 0 | 2 | 4 | 4 | 1 | 5 |
| 44 | 125 | 0 | 3 | 4 | 2 | 2 | 4 |
|    | 250 | 0 | 5 | 5 | 5 | 4 | 5 |
| 45 | 125 | 0 | 2 | 4 | 5 | 3 | 5 |
|    | 250 | 0 | 4.5 | 5 | 5 | 3 | 5 |
| 46 | 125 | 0 | 4 | 3 | 5 | 1 | 5 |
|    | 250 | 0 | 4 | 5 | 5 | 1 | 5 |
| 47 | 125 | 0 | 2 | 5 | 5 | 0 | 5 |
|    | 250 | 0 | 5 | 5 | 5 | 2 | 5 |
| 48 | 125 | 0 | 3 | 3 | 5 | 0 | 5 |
|    | 250 | 0 | 5 | 5 | 5 | 0 | 5 |
| 49 | 125 | 0 | 2 | 3 | 5 | 2 | 5 |
|    | 250 | 1 | 4.5 | 5 | 5 | 2 | 5 |
| 50 | 125 | 0 | 3 | 0 | 5 | 1 | 5 |
|    | 250 | 0 | 4 | 5 | 5 | 4 | 5 |
| 51 | 125 | 0 | 3 | 5 | 2 | 0 | 5 |
|    | 250 | 0 | 4 | 5 | 5 | 1 | 5 |
| 52 | 125 | 0 | 0 | 5 | 0 | 0 | 0 |
|    | 250 | 0 | 1 | 5 | 0 | 0 | 3 |
| 53 | 125 | 0 | 2 | 4 | 0 | 0 | 4 |
|    | 250 | 0 | 2 | 4 | 0 | 0 | 4 |
| 54 | 125 | 0 | 1 | 5 | 4 | 0 | 5 |
|    | 250 | 0 | 4.5 | 5 | 5 | 2 | 5 |
| 55 | 125 | 0 | 3 | 5 | 4 | 0 | 5 |
|    | 250 | 0 | 4 | 5 | 5 | 5 | 5 |
| 56 | 125 | 0 | 2 | 5 | 1 | 4 | 5 |
|    | 250 | 0 | 3 | 5 | 5 | 4 | 5 |
| 57 | 125 | 0 | 2 | 5 | 4 | 4 | 5 |
|    | 250 | 0 | 4 | 5 | 5 | 4 | 5 |
| 58 | 125 | 0 | 2 | 4 | 0 | 0 | 1 |
|    | 250 | 0 | 2 | 5 | 0 | 0 | 5 |
| 59 | 125 | 0 | 2 | 4 | 3 | 0 | 0 |
|    | 250 | 0 | 2 | 5 | 3 | 0 | 2 |
| 60 | 125 | 0 | 4 | 4 | 5 | 0 | 5 |
|    | 250 | 0 | 4.5 | 5 | 5 | 4 | 5 |
| 61 | 125 | 0 | 2 | 3 | 3 | 2 | 5 |
|    | 250 | 0 | 4 | 5 | 5 | 2 | 5 |
| 62 | 125 | 0 | 0 | 4 | 0 | 0 | 0 |
|    | 250 | 0 | 3 | 5 | 1 | 0 | 5 |
| 63 | 125 | 0 | 2 | 5 | 0 | 2 | 5 |
|    | 250 | 0 | 4 | 5 | 1 | 2 | 5 |
| 64 | 125 | 0 | 2 | 5 | 5 | 2 | 5 |
|    | 250 | 0 | 4 | 5 | 5 | 2 | 5 |
| 65 | 125 | 0 | 3 | 5 | 5 | 2 | 5 |
|    | 250 | 0 | 3 | 5 | 5 | 2 | 5 |
| 66 | 125 | 0 | 2 | 5 | 5 | 3 | 5 |

TABLE 2-continued

| Compound No. | Amount of Compound g/10a | Damage to Crop Rice | Barn-yard-grass | Small Flower Umbrella-plant | Bul-rush | Mono-choria | Broad-leaved |
|---|---|---|---|---|---|---|---|
| | 250 | 0 | 4 | 5 | 5 | 3 | 5 |
| 67 | 125 | 0 | 3 | 4 | 4 | 1 | 4 |
| | 250 | 0 | 4 | 5 | 5 | 4 | 5 |
| 68 | 125 | 0 | 1 | 3 | 4 | 3 | 5 |
| | 250 | 0 | 3 | 4 | 5 | 3 | 5 |
| 69 | 125 | 0 | 1 | 2 | 5 | 0 | 5 |
| | 250 | 0 | 3 | 5 | 5 | 3 | 5 |
| 70 | 125 | 0 | 4 | 5 | 5 | 1 | 5 |
| | 250 | 0 | 4.5 | 5 | 5 | 3 | 5 |
| 71 | 125 | 0 | 4.5 | 5 | 5 | 3 | 5 |
| | 250 | 0 | 5 | 5 | 5 | 5 | 5 |
| 72 | 125 | 0 | 4 | 5 | 0 | 0 | 3 |
| | 250 | 0 | 4 | 5 | 0 | 0 | 3 |
| 73 | 125 | 0 | 0 | 5 | 0 | 0 | 0 |
| | 250 | 0 | 4 | 5 | 0 | 0 | 0 |
| 74 | 125 | 0 | 3 | 5 | 0 | 2 | 0 |
| | 250 | 0 | 3 | 5 | 0 | 2 | 0 |
| 76 | 125 | 0 | 4 | 5 | 5 | 5 | 5 |
| | 250 | 0 | 5 | 5 | 5 | 5 | 5 |
| 77 | 125 | 0 | 5 | 5 | 5 | 5 | 5 |
| | 250 | 0 | 5 | 5 | 5 | 5 | 5 |
| 78 | 250 | 0 | 2 | 4 | 4 | 2 | 5 |
| | 500 | 0 | 4 | 5 | 5 | 4 | 5 |
| 79 | 125 | 0 | 5 | 5 | 5 | 5 | 5 |
| | 250 | 0 | 5 | 5 | 5 | 5 | 5 |
| 80 | 125 | 0 | 5 | 5 | 5 | 5 | 5 |
| | 250 | 0 | 5 | 5 | 5 | 5 | 5 |
| 81 | 125 | 0 | 2 | 5 | 4 | 2 | 5 |
| | 250 | 0 | 5 | 5 | 5 | 4 | 5 |
| 82 | 250 | 0 | 3 | 2 | 3 | 2 | 4 |
| | 500 | 0 | 4 | 2 | 4 | 3 | 5 |
| 83 | 250 | 0 | 3 | 3 | 3 | 3 | 5 |
| | 500 | 0 | 5 | 5 | 5 | 5 | 5 |
| 84 | 250 | 0 | 3 | 2 | 3 | 3 | 4 |
| | 500 | 0 | 5 | 2 | 5 | 4 | 5 |
| 85 | 125 | 0 | 4 | 5 | 5 | 4 | 5 |
| | 250 | 0 | 5 | 5 | 5 | 5 | 5 |
| 86 | 125 | 0 | 4 | 3 | 5 | 1 | 5 |
| | 250 | 0 | 4 | 5 | 5 | 2 | 5 |
| 87 | 125 | 0 | 4 | 5 | 4 | 1 | 5 |
| | 250 | 0 | 5 | 5 | 5 | 2 | 5 |
| 88 | 250 | 0 | 3 | 5 | 4 | 3 | 5 |
| | 500 | 0 | 5 | 5 | 5 | 5 | 5 |
| 89 | 250 | 0 | 4 | 5 | 5 | 5 | 5 |
| | 500 | 0 | 5 | 5 | 5 | 5 | 5 |
| 90 | 125 | 0 | 4 | 5 | 5 | 3 | 5 |
| | 250 | 0 | 4 | 5 | 5 | 5 | 5 |
| 91 | 250 | 0 | 4 | 5 | 5 | 3 | 5 |
| | 500 | 0 | 5 | 5 | 5 | 5 | 5 |
| 92 | 125 | 0 | 4 | 4 | 5 | 2 | 5 |
| | 250 | 0 | 5 | 5 | 5 | 3 | 5 |
| 93 | 250 | 0 | 3 | 5 | 3 | 2 | 5 |
| | 500 | 0 | 4 | 5 | 3 | 3 | 5 |
| 94 | 125 | 0 | 4 | 5 | 5 | 3 | 5 |
| | 250 | 0 | 5 | 5 | 5 | 4 | 5 |
| 95 | 250 | 0 | 2 | 5 | 4 | 2 | 5 |
| | 500 | 0 | 4 | 5 | 5 | 4 | 5 |
| 96 | 250 | 0 | 4 | 5 | 4 | 3 | 5 |
| | 500 | 0 | 5 | 5 | 5 | 3 | 5 |
| 97 | 250 | 0 | 3 | 5 | 3 | 1 | 4 |
| | 500 | 0 | 5 | 5 | 3 | 2 | 5 |
| 98 | 250 | 0 | 2 | 3 | 0 | 2 | 4 |
| | 500 | 0 | 3 | 5 | 1 | 3 | 4 |
| 99 | 250 | 0 | 3 | 3 | 1 | 3 | 3 |
| | 500 | 0 | 5 | 4 | 3 | 3 | 4 |
| 100 | 250 | 0 | 3 | 4 | 3 | 4 | 5 |
| | 500 | 0 | 4 | 5 | 4 | 4 | 5 |
| 101 | 250 | 0 | 3 | 4 | 3 | 2 | 5 |
| | 500 | 0 | 4 | 5 | 5 | 3 | 5 |
| 102 | 250 | 0 | 5 | 5 | 4 | 3 | 4 |
| | 500 | 0 | 5 | 5 | 5 | 4 | 4 |
| 103 | 250 | 0 | 3 | 5 | 3 | 2 | 3 |
| | 500 | 0 | 4 | 5 | 5 | 4 | 5 |

TABLE 2-continued

| Compound No. | Amount of Compound g/10a | Damage to Crop Rice | Barn-yard-grass | Small Flower Umbrella-plant | Bul-rush | Mono-choria | Broad-leaved |
|---|---|---|---|---|---|---|---|
| 104 | 250 | 0 | 2 | 5 | 2 | 4 | 4 |
|  | 500 | 0 | 4 | 5 | 4 | 5 | 5 |
| 105 | 250 | 0 | 3 | 5 | 2 | 3 | 5 |
|  | 500 | 0 | 4 | 5 | 3 | 4 | 5 |
| 106 | 250 | 0 | 4 | 5 | 2 | 4 | 5 |
|  | 500 | 0 | 5 | 5 | 3 | 5 | 5 |
| 107 | 250 | 0 | 3 | 5 | 2 | 3 | 5 |
|  | 500 | 0 | 5 | 5 | 3 | 3 | 5 |
| 108 | 250 | 0 | 2 | 5 | 1 | 2 | 2 |
|  | 500 | 0 | 2 | 5 | 2 | 4 | 4 |
| 109 | 250 | 0 | 2 | 3 | 2 | 2 | 3 |
|  | 500 | 0 | 2 | 5 | 2 | 4 | 3 |
| 110 | 250 | 0 | 2 | 3 | 3 | 3 | 4 |
|  | 500 | 0 | 3 | 4 | 4 | 4 | 5 |
| 111 | 250 | 0 | 2 | 5 | 2 | 4 | 5 |
|  | 500 | 0 | 2 | 5 | 3 | 4 | 5 |
| 112 | 250 | 0 | 2 | 5 | 2 | 4 | 4 |
|  | 500 | 0 | 2 | 5 | 2 | 5 | 5 |
| 113 | 250 | 0 | 2 | 5 | 2 | 2 | 4 |
|  | 500 | 0 | 2 | 5 | 3 | 3 | 5 |
| 114 | 250 | 0 | 2 | 4 | 2 | 5 | 5 |
|  | 500 | 0 | 2 | 5 | 3 | 5 | 5 |
| 115 | 250 | 0 | 3 | 5 | 2 | 3 | 5 |
|  | 500 | 0 | 4 | 5 | 3 | 5 | 5 |
| 116 | 250 | 0 | 3 | 5 | 3 | 3 | 5 |
|  | 500 | 0 | 5 | 5 | 5 | 5 | 5 |
| 117 | 125 | 0 | 5 | 5 | 5 | 3 | 5 |
|  | 250 | 0 | 5 | 5 | 5 | 4 | 5 |
| 118 | 250 | 0 | 2 | 4 | 2 | 4 | 5 |
|  | 500 | 0 | 3 | 5 | 3 | 5 | 5 |
| 119 | 125 | 0 | 4 | 5 | 5 | 5 | 5 |
|  | 250 | 0 | 5 | 5 | 5 | 5 | 5 |
| 120 | 250 | 0 | 2 | 4 | 1 | 4 | 5 |
|  | 500 | 0 | 2 | 4 | 2 | 5 | 5 |
| 121 | 250 | 0 | 2 | 4 | 3 | 5 | 3 |
|  | 500 | 0 | 2 | 5 | 3 | 5 | 4 |
| 122 | 250 | 0 | 2 | 5 | 3 | 2 | 3 |
|  | 500 | 0 | 3 | 5 | 4 | 3 | 3 |
| 123 | 250 | 0 | 3 | 4 | 2 | 5 | 5 |
|  | 500 | 0 | 3 | 4 | 4 | 5 | 5 |
| 124 | 250 | 0 | 3 | 4 | 1 | 3 | 4 |
|  | 500 | 0 | 3 | 5 | 2 | 5 | 4 |
| 125 | 250 | 0 | 2 | 5 | 1 | 2 | 4 |
|  | 500 | 0 | 3 | 5 | 2 | 3 | 5 |
| 126 | 250 | 0 | 2 | 4 | 1 | 2 | 3 |
|  | 500 | 0 | 3 | 4 | 1 | 2 | 3 |
| 127 | 250 | 0 | 2 | 4 | 1 | 2 | 3 |
|  | 500 | 0 | 2 | 5 | 1 | 2 | 4 |
| 128 | 250 | 0 | 2 | 4 | 1 | 3 | 3 |
|  | 500 | 0 | 3 | 5 | 1 | 4 | 4 |
| 129 | 250 | 0 | 2 | 3 | 1 | 2 | 4 |
|  | 500 | 0 | 2 | 4 | 1 | 3 | 5 |
| 130 | 250 | 0 | 2 | 3 | 2 | 2 | 4 |
|  | 500 | 0 | 3 | 4 | 3 | 3 | 5 |

TABLE 3

| Compound No. | Y | $R^{15}$ | $R^{16}$ | Properties | NMR (60 MHz) (δ ppm, $CCl_4$) | IR ($cm^{-1}$) |
|---|---|---|---|---|---|---|
| 134 | O | $(CH_2)_6$ |  | $n_D^{25}$ 1.5699 | 1.58(8H, br, s), 3.18–3.72(4H, m), 4.34(2H, s), 8.48(1H, s) | 1640 |
| 135 | O | $(CH_2)_5$ |  | $n_D^{25}$ 1.5760 | 1.63(6H, br, s), 3.28–3.68(4H, m), 4.38(2H, s), 8.50(1H, s) | 1645 |
| 137 | S | $C_2H_5$ | $C_2H_5$ | $n_D^{25}$ 1.6201 | 1.20(6H, t, J=7Hz), 3.80(4H, q, J=7Hz), 4.8(2H, s), 8.52(1H, s) | — |
| 138 | S | $i-C_3H_7$ | $i-C_3H_7$ | $n_D^{25}$ 1.5980 | 1.42(12H, d, J=7Hz), 4.22–5.0(4H, m), 8.56 (1H, s) | — |
| 139 | S | $(CH_2)_5$ |  | $n_D^{25}$ 1.6453 | 1.65(6H, br, s), 4.00(4H, br, s), 4.82(2H, s), 8.57(1H, s) | — |

TABLE 3-continued

| Compound No. | Y | R[15] | R[16] | Properties | NMR (60 MHz) (δ ppm, CCl$_4$) | IR (cm$^{-1}$) |
|---|---|---|---|---|---|---|
| 140 | S | (CH$_2$)$_6$ | | $n_D^{25}$ 1.6292 | 1.52(8H, br, s), 3.82(2H, t, J=7Hz), 4.11(2H, t, J=7Hz), 4.84(2H, s), 8.58(1H, s) | — |
| 141 | O | CH$_3$ \| CH(CH$_2$)$_3$CH \| CH$_3$ | | $n_D^{25}$ 1.5625 | 1.21(6H, d, J=7Hz), 1.41–1.74(6H, m), 4.32 (4H, m), 8.48(1H, s) | 1625 |
| 142 | O | CH$_2$CH$_2$OCH$_2$CH$_2$ | | Oil | 3.54(8H, m), 4.35(2H, s), 8.48(1H, s) | 1620 |
| 143 | O | CH$_3$ \| CH$_2$CH$_2$NCH$_2$CH$_2$ | | Oil | 2.19–2.38(7H, m), 3.40(4H, t, J=7Hz), 4.26 (2H, s), 8.44(1H, s) | 1630 |
| 144 | O | CH$_3$ \| CH$_2$CH$_2$CH$_2$CH$_2$CH | | $n_D^{25}$ 1.5659 | 1.16(3H, d, J=8Hz), 1.58(6H, br, s), 2.48–3.21 (2H, m), 3.69–4.68(3H, m), 8.62(1H, s) | 1635 |
| 145 | O | CH$_2$CH$_3$ \| CHCH$_2$CH$_2$CH$_2$CH$_2$ | | $n_D^{25}$ 1.5592 | 1.82(3H, t, J=7Hz), 1.56(6H, br, s), 2.76(2H, m), 3.6–4.5(5H, m), 8.5(1H, s) | 1635 |
| 146 | O | CH$_3$ \| CH$_2$CHCH$_2$CH$_2$CH$_2$ | | $n_D^{25}$ 1.5653 | 0.87(3H, d, J=7Hz), 1.18–2.00(5H, m), 2.17–3.10(2H, m), 3.48–4.25(2H, m), 4.33(2H, s), 8.48(1H, s) | 1640 |
| 147 | O | CH$_3$ | CH$_2$CH$_2$OH | $n_D^{25}$ 1.5819 | 2.98(3H, s), 3.10–3.70(4H, m), 4.28(2H, s), 8.44(1H, s) | 3430 1640 |
| 148 | O | n-C$_4$H$_9$ | n-C$_4$H$_9$ | $n_D^{25}$ 1.5248 | 0.48–1.80(14H, m), 2.92–3.40(4H, m), 4.22(2H, s), 8.38(1H, s) | 1650 |
| 149 | O | CH$_2$CH$_2$OH | CH$_2$CH$_2$OH | $n_D^{25}$ 1.5931 | 3.00–3.76(8H, m), 4.10–4.42(4H, m), 8.72(1H, s), (DMSO-d6) | 3400 1640 |
| 150 | O | i-C$_4$H$_9$ | i-C$_4$H$_9$ | $n_D^{25}$ 1.5246 | 1.84(6H, d, J=7Hz), 1.92(2H, h, J=7Hz), 3.07(4H, d, J=7Hz), 4.28(2H, s), 8.39(1H, s) | 1650 |
| 151 | O | CH$_2$CH=CH$_2$ | CH$_2$CH=CH$_2$ | $n_D^{25}$ 1.5618 | 3.78–4.05(4H, m), 4.33(2H, s), 4.82–6.10(6H, m), 8.45(1H, s) | 1655 |
| 152 | O | s-C$_4$H$_9$ | s-C$_4$H$_9$ | $n_D^{25}$ 1.5557 | 0.88(6H, t, J=7Hz), 1.25(6H, d, J=7Hz), 1.45–2.00(4H, m), 2.70–3.75(2H, m), 4.29(2H, s), 8.42(1H, s) | 1655 |
| 153 | O | CH$_3$ \| CHCH$_2$OCH$_2$CH \| CH$_3$ | | $n_D^{25}$ 1.5572 | 1.15(6H, d, J=7Hz), 2.29–2.82(2H, m), 2.90–4.20(4H, m), 4.38(2H, s), 8.48(1H, s) | 1660 |
| 154 | O | CH$_3$ \| CH$_2$CH$_2$CHCH$_2$CH$_2$ | | $n_D^{25}$ 1.5658 | 0.90(2H, d, J=6Hz), 1.07–1.89(5H, m), 2.48–3.10(2H, m), 3.68–4.45(4H, m), 8.45(1H, s) | 1650 |
| 155 | O | CH$_3$ \| CH$_2$CHCH$_2$CHCH$_2$ \| CH$_3$ | | $n_D^{25}$ 1.5596 | 1.85(6H, d, J=7Hz), 1.15–2.56(6H, m), 2.80–4.50(4H, m), 8.42(1H, s) | 1660 |
| 156 | O | n-C$_4$H$_9$ | n-C$_6$H$_{13}$ | $n_D^{25}$ 1.5269 | 0.67–1.80(18H, m), 2.92–3.47(4H, m), 4.30 (2H, s), 8.45(1H, s) | 1655 |
| 157 | O | C$_2$H$_5$ | n-C$_4$H$_9$ | $n_D^{25}$ 1.5408 | 0.67–1.81(10H, m), 3.32(4H, q, J=7Hz), 4.32 (2H, s), 8.46(1H, s) | 1650 |
| 158 | O | COOH \| CHCH$_2$CH$_2$CH$_2$ | | $n_D^{25}$ 1.5612 | 1.62–2.49(4H, m), 3.07–3.86(2H, m), 4.21–4.72(3H, m), 8.52(1H, s), 9.96(1H, br, s) | 3000, 1730, 1650 |
| 159 | O | CH$_3$ | n-C$_4$H$_9$ | $n_D^{25}$ 1.5458 | 0.65–1.80(7H, m), 2.87(3H, s), 3.0–3.52(2H, m), 4.29(2H, s), 8.43(1H, s) | 1660 |
| 160 | O | CH$_3$ | n-C$_6$H$_{13}$ | $n_D^{25}$ 1.5336 | 0.6–1.82(11H, m), 2.90(3H, s), 3.02–3.48(2H, m), 8.45(1H, s) | 1660 |
| 161 | O | CH$_3$ | c-C$_7$H$_{13}$ | $n_D^{25}$ 1.5639 | 1.0–2.0(12H, br, s), 2.79(3H, s), 3.57–4.22 (1H, m), 4.34(1H, s), 8.51(1H, s) | 1650 |
| 162 | O | CH$_3$ | c-C$_6$H$_{11}$ | $n_D^{25}$ 1.5687 | 0.84–2.00(10H, m), 2.83(3H, s), 3.62–4.15 (1H, m), 4.32(2H, s), 8.49(1H, s) | 1630 |
| 163 | O | C$_2$H$_5$ | c-C$_6$H$_{11}$ | $n_D^{25}$ 1.5515 | 0.69–2.04(13H, m), 3.30(2H, q, J=7Hz), 3.60–4.16(1H, m), 4.35(2H, s), 8.48(1H, s) | 1650 |
| 164 | O | n-C$_3$H$_7$ | n-C$_3$H$_7$ | $n_D^{25}$ 1.5362 | 0.77(6H, t, J=7Hz), 1.48(4H, h, J=7Hz), 3.16 (4H, t, J=7Hz), 4.23(2H, s), 8.40(1H, s) | 1660 |
| 165 | O | CH$_3$ | (CH$_2$)$_3$OCH$_3$ | $n_D^{25}$ 1.5471 | 1.43–2.0(2H, m), 2.9(3H, s), 3.07–3.58(7H, m), 4.31(2H, s), 8.44(1H, s) | 1660 1120 |
| 166 | O | CH$_3$ | (CH$_2$)$_3$OC$_2$H$_5$ | $n_D^{25}$ 1.5379 | 1.10(3H, t, J=6H), 1.76(2H, q, J=6Hz), 2.91 (3H, s), 3.18–3.62(6H, m), 4.35(2H, s), 8.49 (1H, s) | 1665 1120 |
| 167 | O | CH$_3$ | (CH$_2$)$_3$OPri | $n_D^{25}$ 1.5245 | 1.05(6H, d, J=7Hz), 1.70(2H, q, J=7Hz), 2.90 (3H, s), 3.09–3.63(7H, m), 4.30(2H, s), 8.41 | 1660 1080 |

TABLE 3-continued

| Compound No. | Y | R¹⁵ | R¹⁶ | Properties | NMR (60 MHz) (δ ppm, CCl₄) | IR (cm⁻¹) |
|---|---|---|---|---|---|---|
| | | | | | (1H, s) | |
| 168 | O | CH₃ | (CH₂)₂OEt | $n_D^{25}$ 1.5420 | 1.15(3H, t, J=7Hz), 3.02(3H, s), 3.22–3.65 (6H, m), 4.36(2H, s), 8.48(1H, s) | 1660 1120 |
| 169 | O | CH₃ | c-C₆H₉ | Oil | 1.0–2.1(8H, br, s), 2.77(3H, s), 4.1–4.8(3H, m), 8.48(1H, s), (CDCl₃) | 1650 |
| 170 | O | C₂H₅ | i-C₄H₉ | Oil | 0.91(6H, d, J=7Hz), 1.18(3H, t, J=7Hz), 2.00 (1H, h, J=7Hz), 3.18(2H, d, J=7Hz), 3.41(2H, q, J=7Hz), 4.45(2H, s), 8.52(1H, s), (CDCl₃) | 1660 |
| 171 | O | n-C₃H₇ | n-C₄H₉ | Oil | 0.65–1.95(12H, m), 2.90–3.55(4H, m), 4.35 (2H, s), 8.49(1H, s), (CDCl₃) | 1660 |
| 172 | O | i-C₃H₇ | n-C₄H₉ | Oil | 0.63–1.85(13H, m), 2.84–3.40(2H, m), 3.70–4.5(3H, m), 8.47(1H, s), (CDCl₃) | 1650 |
| 173 | O | s-C₄H₉ | n-C₄H₉ | $n_D^{25}$ 1.5321 | 0.65–1.90(14H, m), 2.85–3.37(2H, m), 3.66–4.21(1H, m), 4.32(2H, s), 8.47(1H, s) | 1650 |
| 174 | O | n-C₃H₇ | i-C₃H₇ | $n_D^{25}$ 1.5494 | 0.75–1.82(11H, m), 2.92–3.41(2H, m), 3.85–4.58(3H, m), 8.51(1H, s) | 1645 |
| 175 | O | i-C₃H₇ | s-C₄H₉ | $n_D^{25}$ 1.5332 | 0.80–2.40(15H, m), 3.08(2H, d, J=7Hz), 3.30–4.02(1H, m), 4.39(2H, s), 8.50(1H, s) | 1650 |
| 176 | O | n-C₃H₇ | s-C₄H₉ | Oil | 0.7–2.0(13H, m), 2.9–3.35(2H, m), 3.60–4.30 (1H, m), 4.42(2H, s), 8.50(1H, s), (CDCl₃) | 1650 |
| 177 | O | CH₃ | i-C₄H₉ | Oil | 0.85(6H, d, J=7Hz), 1.15–2.35(1H, m), 2.70–3.38(5H, m), 4.38(2H, s), 8.48(1H, s) | 1660 |

TABLE 4

| Compound No. | Amount of Compound g/10a | Damage to Crop Rice | Herbicidal Effect | | | | |
|---|---|---|---|---|---|---|---|
| | | | Barnyard-grass | Small Flower Umbrella-plant | Bulrush | Monochoria | Broad-leaved |
| 131 | 250 | 0 | 5 | 5 | 4 | — | 4 |
| | 125 | 0 | 4 | 5 | 4 | — | 4 |
| 132 | 250 | 0 | 3 | 4 | 4 | 3 | 4 |
| | 125 | 0 | 2 | 4 | 3 | 3 | 4 |
| 133 | 125 | 0 | 5 | 5 | 5 | 5 | 5 |
| | 60 | 0 | 5 | 5 | 5 | 5 | 5 |
| 134 | 125 | 0 | 5 | 5 | 4 | 5 | 5 |
| | 60 | 0 | 5 | 5 | 4 | 5 | 5 |
| 135 | 250 | 0 | 3 | 5 | 3 | — | 4 |
| | 125 | 0 | 3 | 4 | 2 | — | 3 |
| 138 | 250 | 0 | 4 | 5 | 4 | — | 4 |
| | 125 | 0 | 3 | 5 | 3 | — | 4 |
| 139 | 250 | 0 | 4 | 5 | 2 | — | 5 |
| | 125 | 0 | 3 | 5 | 2 | — | 4 |
| 140 | 250 | 0 | 3 | 5 | 2 | — | 4 |
| | 125 | 0 | 3 | 5 | 2 | — | 4 |
| 141 | 125 | 0 | 5 | 5 | 3 | 5 | 5 |
| | 60 | 0 | 5 | 5 | 3 | 4 | 5 |
| 144 | 60 | 0 | 5 | 5 | 4 | 3 | 4 |
| | 30 | 0 | 5 | 5 | 3 | 3 | 4 |
| 145 | 125 | 0 | 5 | 5 | 5 | 5 | 5 |
| | 60 | 0 | 5 | 5 | 5 | 5 | 5 |
| 146 | 250 | 0 | 4 | 5 | 4 | 4 | 4 |
| | 125 | 0 | 3 | 5 | 3 | 3 | 4 |
| 148 | 125 | 0 | 5 | 5 | 5 | 4 | 4 |
| | 60 | 0 | 5 | 5 | 4 | 3 | 4 |
| 150 | 250 | 0 | 5 | 5 | 4 | 5 | 4 |
| | 125 | 0 | 5 | 5 | 4 | 4 | 4 |
| 151 | 250 | 0 | 5 | 5 | 4 | 5 | 5 |
| | 125 | 0 | 3 | 4 | 3 | 5 | 4 |
| 152 | 250 | 0 | 5 | 4 | 4 | 4 | 3 |
| | 125 | 0 | 5 | 4 | 3 | 2 | 2 |
| 157 | 125 | 0 | 5 | 5 | 5 | 5 | 5 |
| | 60 | 0 | 5 | 5 | 5 | 5 | 5 |
| 159 | 125 | 0 | 5 | 5 | 5 | 4 | 5 |
| | 60 | 0 | 5 | 5 | 5 | 3 | 5 |
| 160 | 250 | 0 | 5 | 5 | 5 | 5 | 5 |
| | 125 | 0 | 5 | 5 | 5 | 4 | 5 |
| 161 | 250 | 0 | 5 | 5 | 5 | 5 | 5 |
| | 125 | 0 | 5 | 5 | 4 | 5 | 5 |
| 162 | 250 | 0 | 5 | 5 | 5 | 5 | 5 |
| | 125 | 0 | 5 | 5 | 5 | 5 | 5 |

TABLE 4-continued

| Compound No. | Amount of Compound g/10a | Damage to Crop Rice | Herbicidal Effect | | | | |
|---|---|---|---|---|---|---|---|
| | | | Barn-yard-grass | Small Flower Umbrella-plant | Bul-rush | Mono-choria | Broad-leaved |
| 163 | 250 | 0 | 5 | 5 | 5 | 5 | 5 |
| | 125 | 0 | 5 | 5 | 5 | 5 | 5 |
| 164 | 125 | 0 | 5 | 5 | 5 | 5 | 5 |
| | 60 | 0 | 5 | 5 | 4 | 4 | 4 |
| 170 | 250 | 0 | 5 | 5 | 5 | 5 | 5 |
| | 125 | 0 | 4 | 5 | 4 | 5 | 5 |
| 171 | 250 | 0 | 5 | 5 | 5 | 5 | 5 |
| | 125 | 0 | 5 | 5 | 5 | 5 | 5 |
| 172 | 250 | 0 | 5 | 5 | 5 | 5 | 5 |
| | 125 | 0 | 5 | 5 | 5 | 5 | 5 |
| 173 | 125 | 0 | 5 | 5 | 5 | 4 | 5 |
| | 60 | 0 | 3 | 5 | 5 | 2 | 5 |
| 174 | 250 | 0 | 5 | 5 | 5 | 5 | 5 |
| | 125 | 0 | 5 | 5 | 5 | 5 | 5 |
| 175 | 125 | 0 | 5 | 4 | 5 | 4 | 4 |
| | 60 | 0 | 5 | 4 | 4 | 4 | 4 |
| 176 | 125 | 0 | 5 | 5 | 5 | 5 | 4 |
| | 60 | 0 | 5 | 5 | 5 | 3 | 4 |
| 177 | 125 | 0 | 5 | 5 | 5 | 5 | 5 |
| | 60 | 0 | 5 | 5 | 5 | 5 | 5 |

TABLE 5

| Compound No. | Amount of Compound g/10a | Damage to Crop Rice | Herbicidal Effect | | | | |
|---|---|---|---|---|---|---|---|
| | | | Barn-yard-grass | Small Flower Umbrella-plant | Bul-rush | Mono-choria | Broad-leaved |
| 178 | 30 | 0 | 5 | 5 | 5 | 5 | 5 |
| | 15 | 0 | 5 | 5 | 5 | 5 | 5 |
| 179 | 30 | 0 | 5 | 5 | 5 | 5 | 5 |
| | 15 | 0 | 5 | 5 | 5 | 5 | 5 |
| 180 | 30 | 0 | 5 | 5 | 5 | 5 | 5 |
| | 15 | 0 | 5 | 5 | 5 | 5 | 5 |
| 181 | 30 | 0 | 5 | 5 | 5 | 5 | 5 |
| | 15 | 0 | 5 | 5 | 5 | 5 | 5 |
| 182 | 30 | 0 | 5 | 5 | 5 | 5 | 5 |
| | 15 | 0 | 5 | 5 | 5 | 5 | 5 |

TABLE 6

| Compound No. | Amount of Compound g/10a | Damage to Crop Rice | Herbicidal Effect | | | | |
|---|---|---|---|---|---|---|---|
| | | | Barn-yard-grass | Small Flower Umbrella-plant | Bul-rush | Mono-choria | Broad-leaved |
| 183 | 125 | 0 | 4 | 5 | 5 | 5 | 5 |
| | 250 | 0 | 5 | 5 | 5 | 5 | 5 |
| 184 | 250 | 0 | 4 | 5 | 5 | 5 | 5 |
| | 500 | 0 | 5 | 5 | 5 | 5 | 5 |
| 185 | 125 | 0 | 3 | 5 | 5 | 3 | 5 |
| | 250 | 0 | 4 | 5 | 5 | 4 | 5 |
| 186 | 250 | 0 | 4 | 5 | 5 | 4 | 5 |
| | 500 | 0 | 5 | 5 | 5 | 4 | 5 |
| 187 | 250 | 0 | 4 | 3 | 5 | 3 | 5 |
| | 500 | 0 | 5 | 5 | 5 | 4 | 5 |
| 188 | 250 | 0 | 4 | 5 | 4 | 4 | 5 |
| | 500 | 0 | 5 | 5 | 5 | 4 | 5 |

We claim:

1. A thiadiazole compound of the formula:

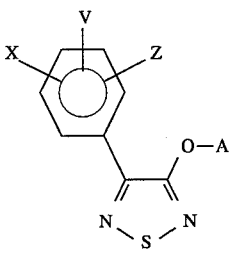

wherein X, V and Z, which may be the same or different, each represent hydrogen, halogen, $C_1$–$C_4$ alkyl, $C_{1-4}$ haloalkyl, $C_1$–$C_4$ alkoxy, hydroxy or nitro, with the proviso that two or three of them cannot simultaneously be hydrogen; A represents hydrogen atom, allyl or propargyl.

2. The thiadiazole compound according to claim 1, wherein A represents hydrogen atom.

3. A thiadiazole compound of the formula:

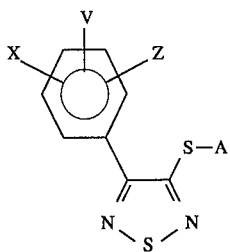

wherein X, V and Z, the same or different, represent hydrogen, halogen, $C_{1-4}$ alkyl, $C_1$–$C_4$ haloalkyl, $C_1$–$C_4$ alkoxy, hydroxy or nitro, with the proviso that two or three of X, V and Z cannot simultaneously be hydrogen; A represents —$SO_2R^1$ (wherein $R^1$ represents $C_1$–$C_4$ alkyl which may be substituted with halogen; a phenyl group which may be substituted with $C_1$–$C_4$ alkyl; or an amino group which is substituted with $C_1$–$C_4$ alkyl); —$CHR^7COR^8$ (wherein $R^7$ represents a hydrogen atom or $C_1$–$C_4$ alkyl, $R^8$ represents a hydroxy group or amino group which may be substituted with a $C_1$–$C_4$ alkyl group, a phenyl group or both); —$C(=W)OR^9$ (wherein W represents an oxygen atom or a sulfur atom, $R^9$ represents $C_1$–$C_4$ alkyl which may be substituted with halogen, ($C_1$–$C_4$) alkoxy ($C_1$–$C_4$) alkyl, benzyl, phenyl, tetrahydrofurfuryl or alkylideneamino group); or —$COR^{10}$ (wherein $R^{10}$ represents phenyl, $C_1$–$C_4$ alkyl, or $C_3$–$C_6$ cycloalkyl which may be substituted with halogen, $C_1$–$C_4$ alkyl, $C_1$–$C_4$ haloalkyl, $C_1$–$C_4$ alkoxy, nitro or with cyano group.

4. The thiadiazole compound according to claim 3, wherein A represents —$SO_2R^1$ ($R^1$ represents $C_1$–$C_4$ alkyl which may be substituted with halogen; a phenyl group which may be substituted with $C_1$–$C_4$ alkyl, or amino group which is substituted with $C_1$–$C_4$ alkyl); or —$CHR^7COR^8$ (wherein $R^7$ represents a hydrogen atom or $C_1$–$C_4$ alkyl, and $R^8$ represents a hydroxy group or amino group which may be substituted with $C_1$–$C_4$ alkyl group and/or with phenyl group).

5. A herbicidal composition comprising as an effective ingredient the thiadiazole compound according to claim 1 together with an agriculturally acceptable carrier.

6. A herbicidal composition comprising as an effective ingredient the thiadiazole compound according to claim 2 together with an agriculturally acceptable carrier.

7. A herbicidal composition comprising as an effective ingredient the thiadiazole compound according to claim 3 together with an agriculturally acceptable carrier.

8. A herbicidal composition comprising as an effective ingredient the thiadiazole compound according to claim 4 together with an agriculturally acceptable carrier.

* * * * *